(12) United States Patent
Strait

(10) Patent No.: US 7,892,511 B2
(45) Date of Patent: Feb. 22, 2011

(54) PSEUDOISOTHERMAL AMMONIA PROCESS

(75) Inventor: Richard B. Strait, Singapore (SG)

(73) Assignee: Kellogg Brown & Root LLC, Houston, TX (US)

( * ) Notice: Subject to any disclaimer, the term of this patent is extended or adjusted under 35 U.S.C. 154(b) by 452 days.

(21) Appl. No.: 12/048,596

(22) Filed: Mar. 14, 2008

(65) Prior Publication Data

US 2008/0161428 A1    Jul. 3, 2008

Related U.S. Application Data

(63) Continuation-in-part of application No. 10/884,323, filed on Jul. 2, 2004, now Pat. No. 7,435,401.

(51) Int. Cl.
*C01C 1/04* (2006.01)
*C07C 27/06* (2006.01)
*C07C 43/04* (2006.01)
*C07C 29/152* (2006.01)
*C07C 69/00* (2006.01)

(52) U.S. Cl. .................. 423/360; 423/361; 423/659; 518/702; 518/703; 560/129; 568/671; 568/840; 568/910; 585/700

(58) Field of Classification Search ............ 252/373; 423/360, 361, 659; 568/840, 910, 671; 560/129; 518/703; 585/700
See application file for complete search history.

(56) References Cited

U.S. PATENT DOCUMENTS

| 1,931,678 A | 10/1933 | Porter |
| 1,938,598 A | 12/1933 | Loud |
| 1,972,937 A | 9/1934 | Jaeger |
| 2,046,478 A | 7/1936 | O'Leary |
| 3,094,391 A | 6/1963 | Mader |
| 3,716,619 A | 2/1973 | Lynn et al. |
| 3,816,513 A | 6/1974 | Wakamatsu et al. |
| 3,970,435 A | 7/1976 | Schultz et al. |
| 4,055,628 A | 10/1977 | McCarroll et al. |

(Continued)

FOREIGN PATENT DOCUMENTS

EP        0 124 226 A2    11/1984

(Continued)

OTHER PUBLICATIONS

Heydorn, E. C., Street, B. T., and Kornosky, R. M., "Liquid Phase Methanol (LPMEOH™ ) Project Operational Experience," (Presented at the Gasification Technology Council Meeting in San Francisco on Oct. 4-7, 1998).

*Primary Examiner*—Wayne Langel
(74) *Attorney, Agent, or Firm*—KBR IP Legal Dept.

(57) ABSTRACT

Systems and processes for producing one or more products from syngas are provided. A feedstock can be gasified in the presence of an oxidant to provide a syngas comprising carbon dioxide, carbon monoxide, and hydrogen. At least a portion of the syngas can be combusted to provide an exhaust gas. At least a portion of the exhaust gas can be introduced to a channel having one or more reaction zones at least partially disposed therein, wherein the one or more reaction zones are in indirect heat exchange with the exhaust gas, wherein the one or more reaction zones comprises one or more catalyst-containing tubes. A reactant can be reacted in at least one of the one or more reaction zones to provide one or more reactor products.

15 Claims, 8 Drawing Sheets

U.S. PATENT DOCUMENTS

| | | | |
|---|---|---|---|
| 4,098,588 A | 7/1978 | Buswell et al. | |
| 4,122,040 A | 10/1978 | McCarroll et al. | |
| 4,163,775 A | 8/1979 | Foster et al. | |
| 4,216,339 A | 8/1980 | Couteau et al. | |
| 4,230,669 A | 10/1980 | Eagle et al. | |
| 4,400,309 A | 8/1983 | McMahon et al. | |
| 4,414,191 A | 11/1983 | Fuderer | |
| 4,568,530 A | 2/1986 | Mandelik et al. | |
| 4,568,531 A | 2/1986 | van Dijk et al. | |
| 4,568,532 A | 2/1986 | Benner et al. | |
| 4,568,663 A | 2/1986 | Mauldin | |
| 4,663,305 A | 5/1987 | Mauldin et al. | |
| 4,666,680 A | 5/1987 | Lewis | |
| 4,696,799 A | 9/1987 | Noe | |
| 4,735,780 A | 4/1988 | Noe | |
| 4,824,658 A | 4/1989 | Karafian et al. | |
| 4,859,214 A * | 8/1989 | Segerstrom et al. | 48/197 R |
| 4,863,707 A | 9/1989 | McShea, III et al. | |
| 4,867,959 A | 9/1989 | Grotz | |
| 4,891,937 A | 1/1990 | Noguchi et al. | |
| 4,959,079 A | 9/1990 | Grotz et al. | |
| 4,963,338 A | 10/1990 | Zardi et al. | |
| 4,992,406 A | 2/1991 | Mauldin et al. | |
| 5,011,625 A | 4/1991 | LeBlanc | |
| 5,075,269 A | 12/1991 | Degnan et al. | |
| 5,122,299 A | 6/1992 | LeBlanc | |
| 5,221,524 A | 6/1993 | Eguchi | |
| 5,250,270 A | 10/1993 | Noe | |
| 5,348,982 A | 9/1994 | Herbolzheimer et al. | |
| 5,545,674 A | 8/1996 | Behrmann et al. | |
| 5,570,578 A | 11/1996 | Saujet et al. | |
| 5,621,155 A | 4/1997 | Benham et al. | |
| 5,736,116 A | 4/1998 | LeBlanc et al. | |
| 5,934,943 A | 8/1999 | McCarthy | |
| 5,945,459 A | 8/1999 | Mauldin | |
| 5,997,834 A | 12/1999 | Udengaard et al. | |
| 6,077,459 A * | 6/2000 | Laursen et al. | 252/376 |
| 6,087,405 A | 7/2000 | Plecha et al. | |
| 6,103,143 A | 8/2000 | Sircar et al. | |
| 6,117,814 A | 9/2000 | Plecha et al. | |
| 6,124,367 A | 9/2000 | Plecha et al. | |
| 6,136,868 A | 10/2000 | Culross et al. | |
| 6,171,570 B1 | 1/2001 | Czuppon | |
| 6,237,545 B1 | 5/2001 | Barnett et al. | |
| 6,284,807 B1 | 9/2001 | Leviness et al. | |
| 6,300,268 B1 | 10/2001 | Lapidus et al. | |
| 6,313,062 B1 | 11/2001 | Krylova et al. | |
| 6,319,960 B1 | 11/2001 | Behrmann et al. | |
| 6,331,575 B1 | 12/2001 | Mauldin | |
| 6,395,251 B1 | 5/2002 | Cotting | |
| 6,534,028 B2 | 3/2003 | von Hippel et al. | |
| 6,682,711 B2 | 1/2004 | Motal et al. | |
| 6,818,028 B2 | 11/2004 | Barnett et al. | |
| 6,848,934 B1 | 2/2005 | McCarthy | |
| 6,955,757 B1 | 10/2005 | Speth | |
| 7,012,103 B2 | 3/2006 | Espinoza et al. | |
| 7,435,401 B2 * | 10/2008 | Barnett et al. | 423/360 |
| 7,513,919 B2 | 4/2009 | Barnett et al. | |
| 2002/0031455 A1 * | 3/2002 | Hippel et al. | 422/173 |
| 2002/0085970 A1 | 7/2002 | Sederquist et al. | |
| 2003/0110694 A1 | 6/2003 | Drnevich et al. | |
| 2005/0284797 A1 | 12/2005 | Genetti et al. | |
| 2006/0149423 A1 | 7/2006 | Barnicki et al. | |

FOREIGN PATENT DOCUMENTS

| | | |
|---|---|---|
| EP | 0 437 059 A2 | 7/1991 |
| EP | 0 440 258 A2 | 7/1991 |
| EP | 0 855 366 A1 | 7/1998 |

* cited by examiner

PSEUDOISOTHERMAL AMMONIA PROCESS

CROSS-REFERENCE TO RELATED APPLICATIONS

This application is a continuation-in-part of U.S. patent application having Ser. No. 10/884,323, filed on Jul. 2, 2004, now U.S. Pat. No. 7,435,401 which is incorporated by reference herein.

BACKGROUND

1. Field

The present embodiments generally relate to systems and processes for producing syngas and chemicals.

2. Description of the Related Art

Ammonia is commonly manufactured by reacting synthesis gas (syngas) components nitrogen and hydrogen in an ammonia synthesis loop including a compressor, an ammonia synthesis reactor, ammonia condensation and recovery units, and purge gas recovery. After a pass through the ammonia synthesis reactor, the unreacted synthesis gas components are typically recovered and recycled to the compressor and the reactor in a loop. Make-up synthesis gas can be continuously added to the ammonia synthesis loop to provide fresh hydrogen and nitrogen.

Synthesis gas typically contains inert components introduced with the make-up syngas, including argon, methane, carbon dioxide, and others that do not contribute to ammonia production and undesirably accumulate in the loop. Therefore, a purge gas stream can be taken from the ammonia synthesis loop to avoid an excessive concentration of the inerts in the loop. The purge stream can typically be processed in a hydrogen recovery unit, yielding a waste gas stream and a hydrogen-enriched stream for recycle to the ammonia synthesis loop. The waste gas stream comprises principally nitrogen with minor amounts of carbon dioxide, methane, hydrogen, and argon. In some cases, the waste gas can be used as a low heating value fuel gas.

A significant technological advance in the manufacture of ammonia has been the use of highly active synthesis catalysts comprising a platinum group metal such as ruthenium on a graphite-containing support, as described in U.S. Pat. Nos. 4,055,628, 4,122,040 and 4,163,775. Also, reactors have been designed to use this more active catalyst, such as a catalytic reactor bed disclosed in U.S. Pat. No. 5,250,270. Other ammonia synthesis reactors include those disclosed in U.S. Pat. Nos. 4,230,669, 4,696,799, and 4,735,780.

Ammonia synthesis schemes have also been developed based on the highly active synthesis catalyst. U.S. Pat. No. 4,568,530 discloses reacting a stoichiometrically hydrogen-lean synthesis gas in an ammonia synthesis reactor containing a highly active catalyst in the synthesis loop.

U.S. Pat. No. 4,568,532 discloses an ammonia synthesis reactor, based on a highly active catalyst, installed in series in the ammonia synthesis loop downstream from a reactor containing a conventional iron-based synthesis catalyst.

U.S. Pat. No. 4,568,531 discloses introducing a purge stream from a primary synthesis loop into a second synthesis loop using a more active synthesis catalyst to produce additional ammonia from the purge stream. Another purge stream, significantly reduced in size, can be taken from the second synthesis loop to avoid an excessive buildup of inerts. The second synthesis loop, like the primary ammonia synthesis loop, employs a recycle compressor to recycle synthesis gas to the active catalyst reactors in the second synthesis loop.

U.S. Pat. No. 6,171,570 discloses converting hydrogen and nitrogen into additional ammonia from a purge stream from an ammonia synthesis loop, using an ammonia synthesis reactor that does not require staged cooling. In particular, ammonia synthesis loop purge gas can be provided to an inlet of a shell and tube reactor having an ammonia synthesis catalyst on the tube-side, while boiler feedwater (BFW) can be supplied to the shell-side of the reactor to provide cooling and/or to generate steam.

U.S. Patent Application Publication 20030027096, Barnett et al., describes a method to increase reforming furnace efficiency by preheating a reagent stream and generating synthesis gas in catalytic reactors heated in radiant, transition, and convective sections of a steam-methane reforming furnace.

Patents and publications referred to herein are hereby incorporated by reference in their entireties.

BRIEF DESCRIPTION OF THE DRAWINGS

So that the manner in which the above recited features of the present invention can be understood in detail, a more particular description of the invention may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
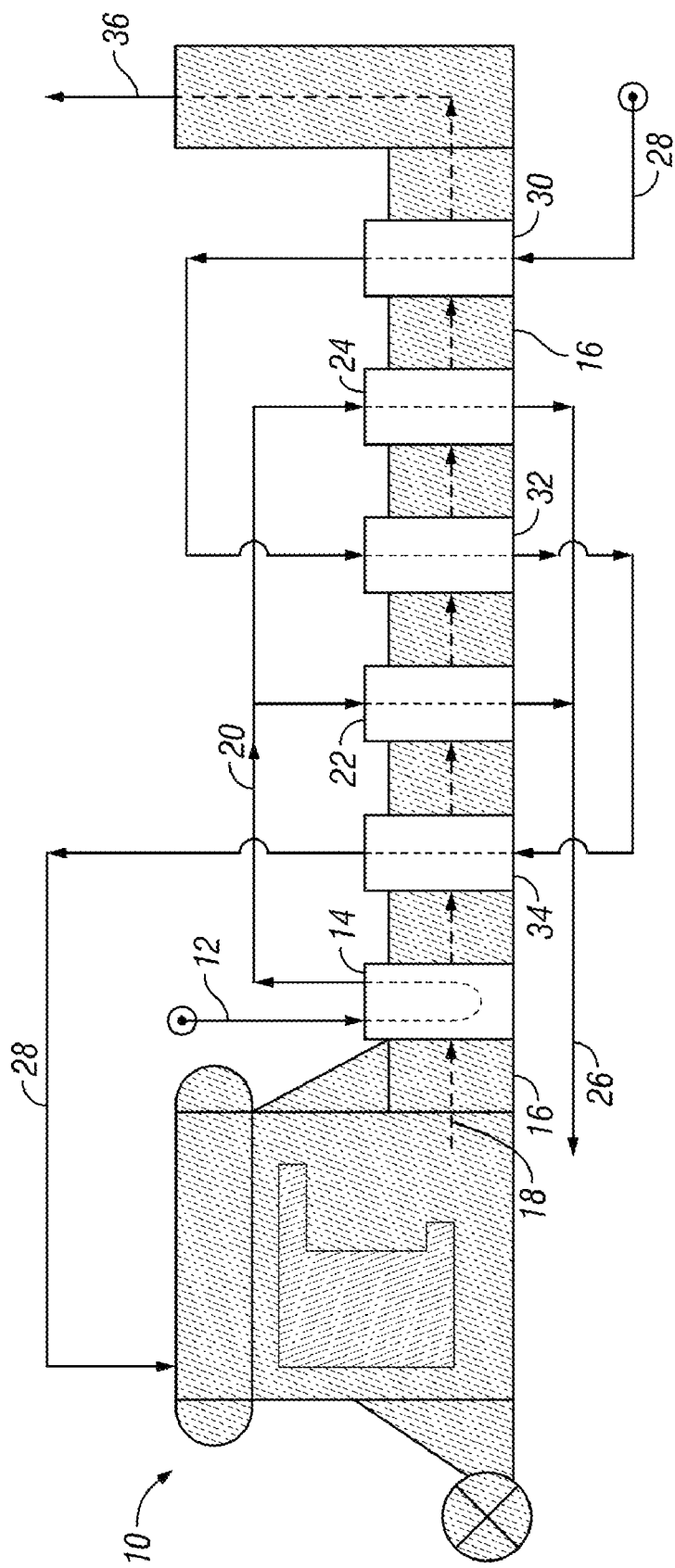
FIG. 1 is a schematic for the conversion of hydrogen and nitrogen in parallel reactors positioned in series in the flow of an exhaust gas stream from a package boiler.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

A process to convert nitrogen and hydrogen to ammonia is provided. An exothermic catalytic reactor can be placed in a hot gas duct of a combustion unit, for example a gas turbine, package boiler, air preheater, primary reformer, or any other fired heater or equipment that may be available. Heat can be transferred from the ammonia reactor to heat the hot gas, such that pseudoisothermal reaction conditions can be approached in the reactor, for example the temperature increase of the reactants between the inlet and outlet of the reactor can be limited to less than 100° C.

The feed stream of hydrogen and nitrogen can be supplied to an inlet of at least one ammonia synthesis reactor comprising a plurality of catalyst-containing reactor tubes. The feed stream passes through the synthesis reactor tubes, to form a product gas having increased ammonia content relative to the feed stream. The synthesis reaction can be exothermic. The reactor tubes penetrate the hot gas duct such that the hot gas flows across the reactor tubes, dissipating reaction heat into the hot gas and maintaining pseudoisothermal reactor conditions. The heat imparted to the combustion unit gas can be recovered by heating boiler feed water (BFW) for steam generation, preheating combustion air or a feed stream to a synthesis gas reactor, heating a process stream, or the like, using heat recovery equipment typically found in hot gas ducts associated with the combustion unit.

By operating at a nearly constant temperature, the reaction has a closer approach to equilibrium, which in turn requires less catalyst for the reaction. In addition, the dissipation of heat decreases the chances for hot spots in the reactor and prolongs catalyst life.

Additionally, unlike conventional shell-and-tube synthesis reactor systems, the method can provide for leaks from duct-installed synthesis reactor tubes, steam coils, and process heat exchangers or BFW coils to pass into the exhaust gas and be controlled or vented. This substantially minimizes any risk of cross-contamination between process streams. Moreover, since boiler feedwater at elevated pressure can be not used as a reactor-cooling medium in contact with the reactor tubes, there can be minimal risk of catalyst poisoning from the BFW in the event of a breach of a reactor tube wall.

The feed to the ammonia synthesis reactor can comprise a stream including nitrogen and hydrogen at reactable concentrations, such as a synthesis gas, recycle syngas, or ammonia synthesis loop purge gas.

The catalyst used in the ammonia synthesis reactor can be a conventional ammonia conversion catalyst such as magnetite. Additionally, a high-activity catalyst can be used, such as a catalyst of group VIII, or the platinum group metals, such as ruthenium.

Pseudoisothermal ammonia conversion can be used in a secondary synthesis loop of an ammonia synthesis unit to form ammonia from a purge gas stream from the primary loop. Ammonia production can thereby be maximized and waste gas rejection can be minimized. Alternatively, pseudoisothermal ammonia conversion can be utilized in a primary ammonia synthesis loop. A plurality of ammonia synthesis reactors can be used in combination, comprising one or more catalysts. For example, a synthesis reactor using a high-activity catalyst can be configured downstream of a reactor containing magnetite catalyst. The magnetite-containing reactor acts as a guard bed for the high-activity catalyst in the downstream reactor. As a result, the high-activity catalyst can be used in a relatively coarse size form, particularly to reduce dynamic pressure drop in the synthesis loop.

As one example, ammonia synthesis reactors can be disposed in the convection section of a hydrocarbon reforming furnace, alone or in combination with a syngas pre-reformer. The pre-reformer, desirably disposed in a transition section of the reforming furnace as described in patent application publication US 20030027096, Feb. 6, 2003, Barnett, et al., which is hereby incorporated herein by reference in its entirety, partially cools the exhaust gas through the transition section. At least one synthesis reactor in communication with the reformer convection section further cools the partially cooled exhaust gas leaving the transition section Generally, initial design of a plant with a primary ammonia synthesis loop can be configured in cooperative combination with a secondary synthesis reaction. Secondary synthesis can be applied in a purge gas loop to further convert residual nitrogen and hydrogen to additional ammonia. The design methodology of this arrangement can be also advantageously applied in the retrofit of an existing ammonia plant having only a primary synthesis loop, or to replace a poorly performing secondary synthesis loop reactor.

In one embodiment as shown in the package boiler 10 seen in FIG. 1, a purge gas feed stream 12 containing nitrogen and hydrogen can be heated in exchanger 14 mounted in an exhaust duct 16 for the boiler exhaust gas 18. Preheated feed stream 20 can then fed to catalyst-containing tubes in parallel ammonia synthesis reactors 22, 24. Reactor effluent 26 flows downstream to conventional ammonia recovery (not shown). Boiler feedwater (BFW) can be supplied through line 28 successively to BFW heating units 30, 32, and 34. BFW heaters 30, 32 can be positioned downstream from the respective reactors 24, 22 to recover heat from the exhaust gas flow 18 at elevated temperatures. BFW heater 32 thus functions as an interstage cooler between the upstream and downstream reactors 22, 24 so that the temperature conditions, flow rates and conversion rates in the parallel reactors 22, 24 can be essentially equivalent. Cooled exhaust gas 36 flows downstream from the BFW heater 30 for conventional processing.

Reactions in the purge gas synthesis reactors 22, 24 can be constrained to pseudoisothermal conditions by heating the exhaust gas 18 to remove the heat of reaction. The exhaust gas 18 serves as a common heat transfer medium, successively alternating between heat removal from exothermic reactors 22, 24 and heat recovery to the exchangers 14, 30, 32, 34.

The reactors 22, 24 can be designed to specific applications and purposes by taking into account the flow rates of syngas 12 and exhaust gas 18, tube surface area, heat transfer coefficients, stream residence times, dynamic pressure losses, conversion rates, and like design factors. The pseudoisothermal temperature rise ($\Delta T$) in the syngas 12 can be less than 80° C., and more desirably less than 50° C. The limits of operating temperature in the synthesis reactors 24 are in general from 300° to 650° C., and desirably from 370° to 480° C. The exhaust gas 18 can have a temperature less than the desired reaction temperature, but the temperature should not be so low that the reaction temperature anywhere in the reactor is less than the syngas feed temperature, taking into account the flow rates of each. Pseudoisothermal conditions and startup can be facilitated by using hot gas for reactor cooling at a minimum temperature of 300° C.

As nitrogen and hydrogen in the feed stream 12 are converted in the reactor tubes 22, 24, ammonia concentration in the stream increases. The purge gas feed stream can have ammonia concentrations in a range of up to 10 volume percent, and the product stream 26 from 10 to 40 volume percent.

Undesirable mechanical design elements seen in conventional synthesis reactors can be avoided. The process can be simple in contrast to conventional ammonia synthesis reactors typically embodying a complex design as a shell-and-tube exchanger wherein synthesis gas passes shell side sequentially through multiple radial and/or axial flow reactor stages housed in a high-pressure vessel for preheating the syngas and interstage cooling of intermediate reactor effluents. In contrast to isothermal operation with boiler feed water as a heat transfer medium employing elevated pressures, such as, for example, from 6.8 to 10.3 MPa, the process can use inexpensive low-pressure vessel designs for the heat removal media.

Figure 2:
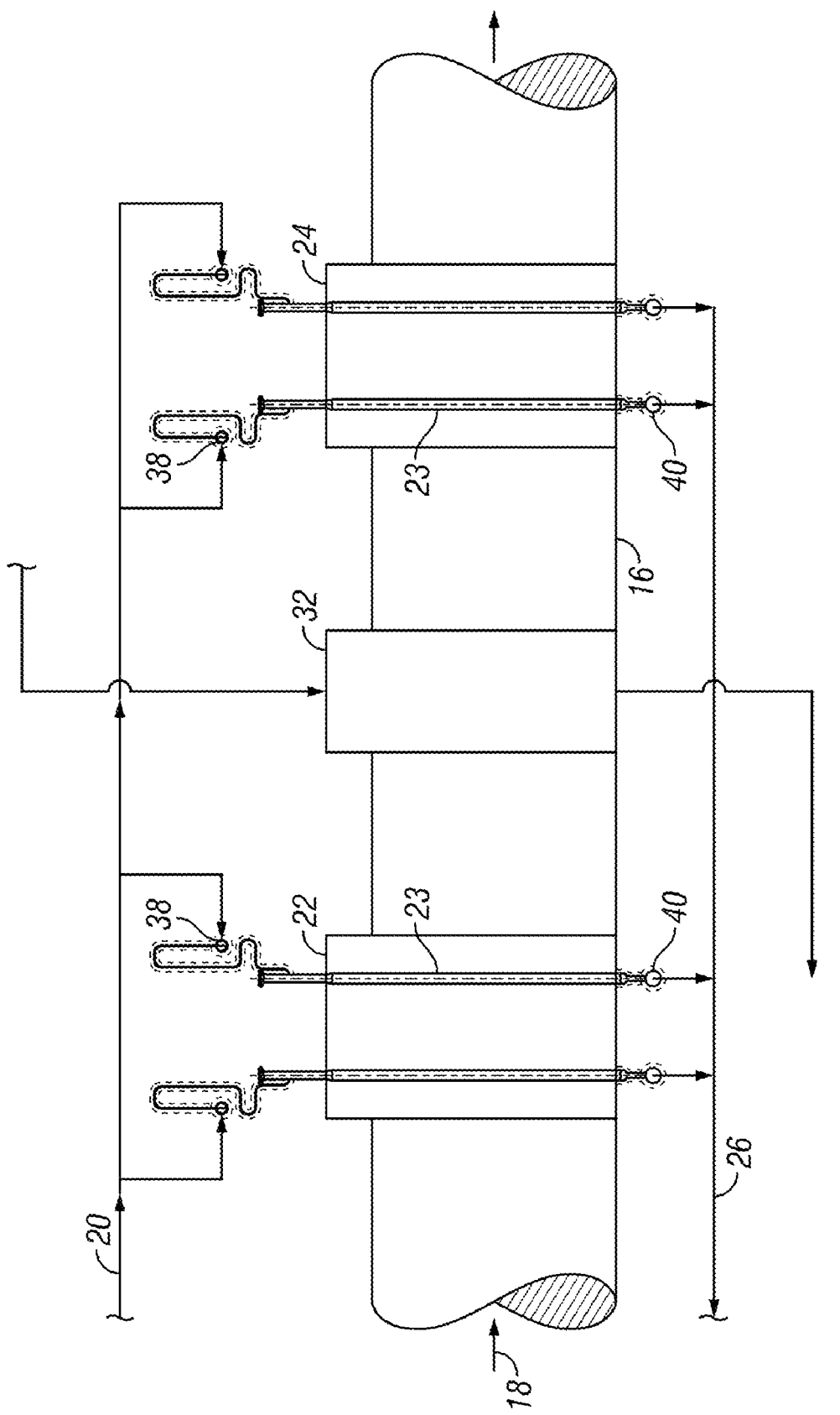
FIG. 2 is an expanded view of section 2 in FIG. 1.

FIG. 2 shows an enlarged vertical arrangement of reactor tubes 23 disposed in two transverse rows within the synthesis reactors 22, 24 installed in the exhaust gas duct 16 of FIG. 1. The number of tubes 23 depends on the desired tube size and design throughput rates of syngas 20. The tubes 23 may be oriented vertically or horizontally, or at oblique angles. In the illustrated embodiment, the tubes 23 are oriented vertically to facilitate catalyst loading and removal. Inlet manifolds 38 distribute the syngas feed stream 20 from a common header into the catalyst-filled tubes 23. Outlet manifold 40 gathers the ammonia-rich effluent exiting the catalyst tubes 23 into product stream 26.

The outlet manifold 40 can support the tubes 23 at lower ends thereof. The outlet manifold 40 can in turn be supported by structural members (not shown) on either side of the ammonia synthesis reactors 22, 24. It can be desirable to orient the reactor tubes transversely, e.g. perpendicularly, with respect to the flow of the exhaust gas 18 through the exhaust duct 16 to maximize heat transfer coefficients and improve temperature differences between the syngas and the exhaust gas.

Figure 3:
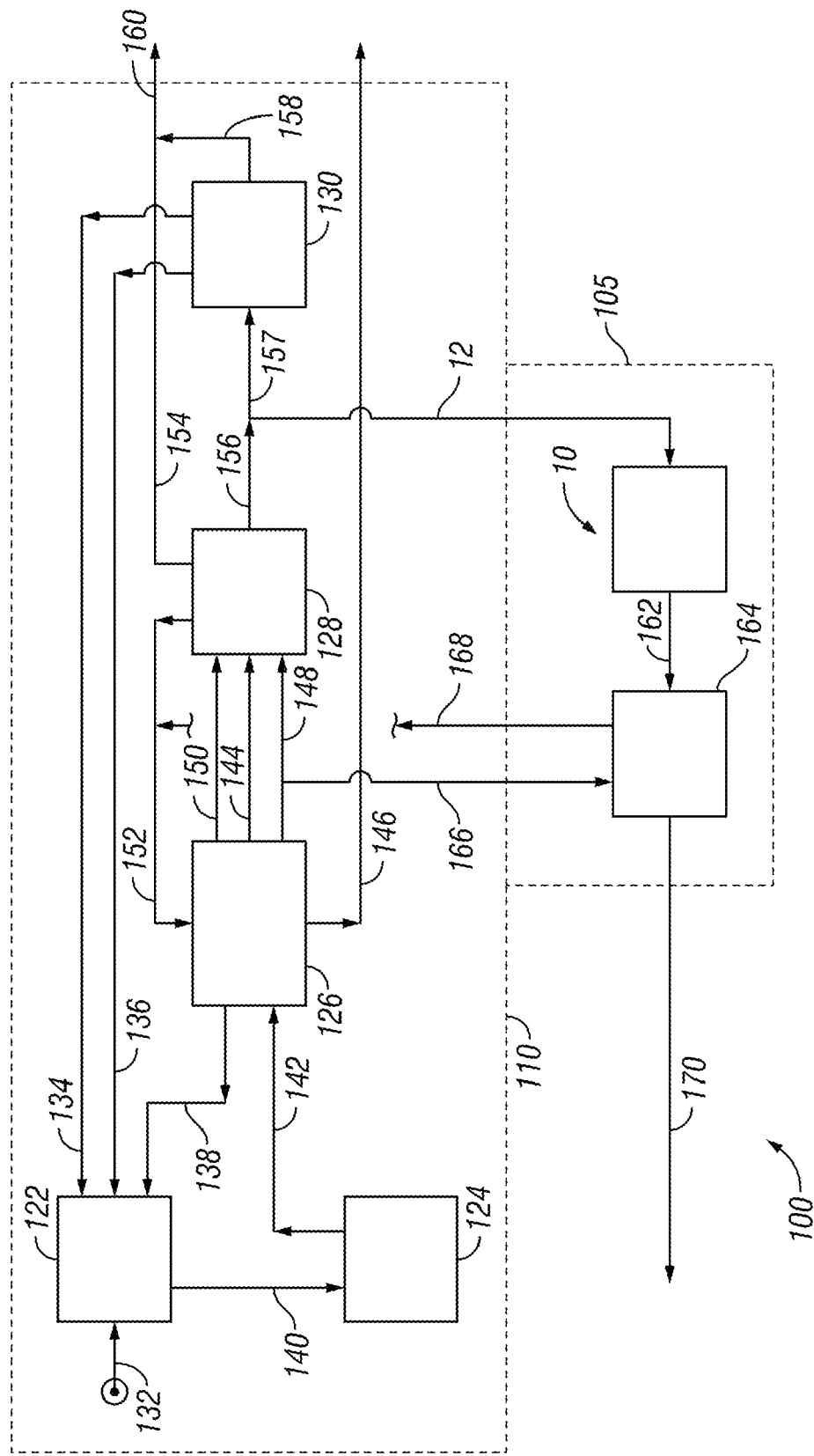
FIG. 3 is a block diagram of a primary synthesis loop configured with a secondary synthesis loop.

FIG. 3 is a schematic for an ammonia plant 100 incorporating secondary ammonia synthesis 105 integrated with a primary ammonia synthesis loop 110. The primary ammonia loop 110 includes syngas compression 122, primary ammonia synthesis 124, ammonia condensation and purification 126, ammonia recovery 128, and hydrogen recovery 130, all of which are generally well known in the art. Briefly, a makeup syngas stream 132 of nitrogen and hydrogen has a purity from about 95 to 100 volume percent, typically from 97.5 to 99.5 volume percent. Compression 122 supplies the makeup syngas 132 and recirculated syngas 138 at a suitable pressure for ammonia synthesis. Syngas stream 140 can be introduced to primary ammonia synthesis 124, and ammonia-rich product gas 142 flows to unit 126 for nearly isobaric stagewise refrigeration and condensation. Ammonia-lean syngas vapor 138 can be recirculated to compression 122 as previously mentioned, and a slipstream 144 of the ammonia-lean syngas vapor can be diverted to high-pressure ammonia recovery 128 to separate water vapor and noncondensable gases. Condensate formed in equilibrium with the recycle vapor 138 can be used as makeup refrigerant in the condensation/purification system 126. The refrigerant cyclically condenses and flashes through a plurality of stages (not shown) within condensation/purification 126, yielding a purified ammonia stream 146, in a manner well known in the art.

A slipstream 148 of partially purified ammonia refrigerant can be diverted to ammonia recovery 128 for use as makeup liquid to ammonia distillation. A flashed refrigerant slip stream 150 comprising low-pressure ammonia plus noncondensable gases and other vapor from the refrigeration can be diverted to ammonia recovery 128 to separate water vapor and noncondensable gases. Ammonia recovery 128 returns an upgraded, low-pressure ammonia vapor stream 152 to the refrigeration subsystem. Ammonia recovery 128 produces a low-pressure waste gas stream 154, typically at a low mass flow rate of about 0.1 to 0.5 percent of the mass flow rate of makeup syngas 132.

A high-pressure purge gas stream 156 can be taken from ammonia purification 128 to remove inert gases such as argon, carbon dioxide, and methane that accumulate in the primary synthesis loop. A portion 157 of the purge gas 156 can be sent to conventional hydrogen recovery 330. The hydrogen can be recovered as low-pressure hydrogen stream 134 and high-pressure hydrogen stream 136 that can be recycled with the syngas to compression 122 and ammonia synthesis 124. Waste gas comprising primarily nitrogen, plus argon, carbon dioxide, and methane in minor proportions flows through line 158 and together with waste gas stream 154 to stream 160.

Another portion of the purge gas 156 can be supplied as a feed 12 to secondary synthesis 105, which includes a pseudo-isothermal converter in package boiler unit 10, as described above in reference to FIGS. 1 and 2, that produces an ammonia-rich effluent for feed to ammonia recovery system 164, which can be as discussed and described in more detail below with reference to FIG. 4. The secondary recovery 164 imports partially purified ammonia refrigerant 166 from condensation/purification 126 as makeup liquid for ammonia distillation, and returns a high-concentration ammonia vapor stream 168 to stream 152. Ammonia-lean stream 170 comprises nitrogen and hydrogen and at high pressure, and if desired can be recycled to reformer feed, desirably upstream of a mixed-feed preheat coil.

In operation, the secondary synthesis improves plant productivity by: (1) increasing ammonia production, (2) reducing syngas makeup demand, and (3) reducing purge gas losses. Ammonia conversion in the secondary synthesis can be from about 5 to 20 percent, for example 10 to 15 percent, of the feed 12.

The purge gas stream 157 in a primary ammonia synthesis loop without secondary ammonia conversion typically has a mass flow rate equivalent to about 15 to 25 percent of the mass flow rate of the makeup syngas 132. In contrast, purge gas flowrates obtained by implementing the secondary synthesis can be reduced in a range of 35 to 65 percent, desirably by about 50 percent. Waste gas 160 can be reduced by up to 10 to 15 percent, desirably from 5 to 10 percent. Hydrogen recovery rates via recycle streams 134, 136 remain at about 60 to 80 percent of the hydrogen in the purge gas 157, usually about 70 to 75 percent.

Figure 4:
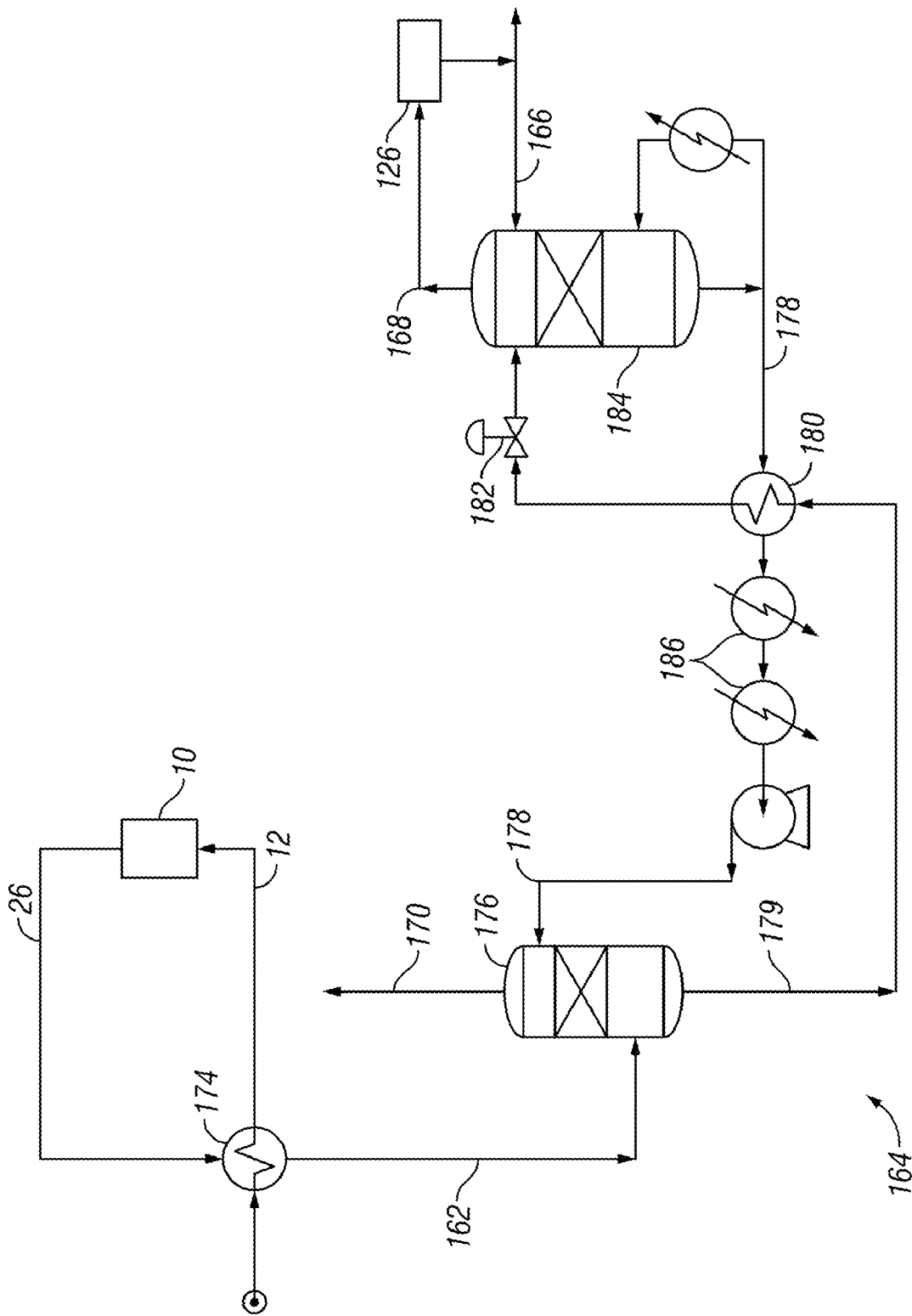
FIG. 4 is a schematic of secondary ammonia synthesis from a purge gas.

With reference to the embodiment shown in FIG. 4, high-pressure purge gas in stream 12 can be heated in cross-exchanger 174 for feed to pseudoisothermal ammonia conversion in the exhaust duct of package boiler 10 (see FIGS. 1-2). Ammonia-enriched effluent stream 26 can be cooled in the cross-exchanger 174 and supplied via line 162 to high-pressure scrubber 176 for contact with lean aqueous ammonia liquor stream 178. Ammonia-rich liquor 179 from the scrubber 176 can be reheated in cross-exchanger 180, depressurized across valve 182, and fed to distillation column 184. Distillation column 184 can be refluxed with partially purified ammonia refrigerant via stream 166, and produces overhead stream 168 comprising high-concentration ammonia vapor returned to condensation/purification 126 (see FIG. 3). The bottoms can be cooled in cross-exchanger 180 and one or more exchangers 186 for recirculation via line 178 to the scrubber 176. Ammonia-lean syngas 170 can be discharged overhead from the scrubber 176.

Figure 5:
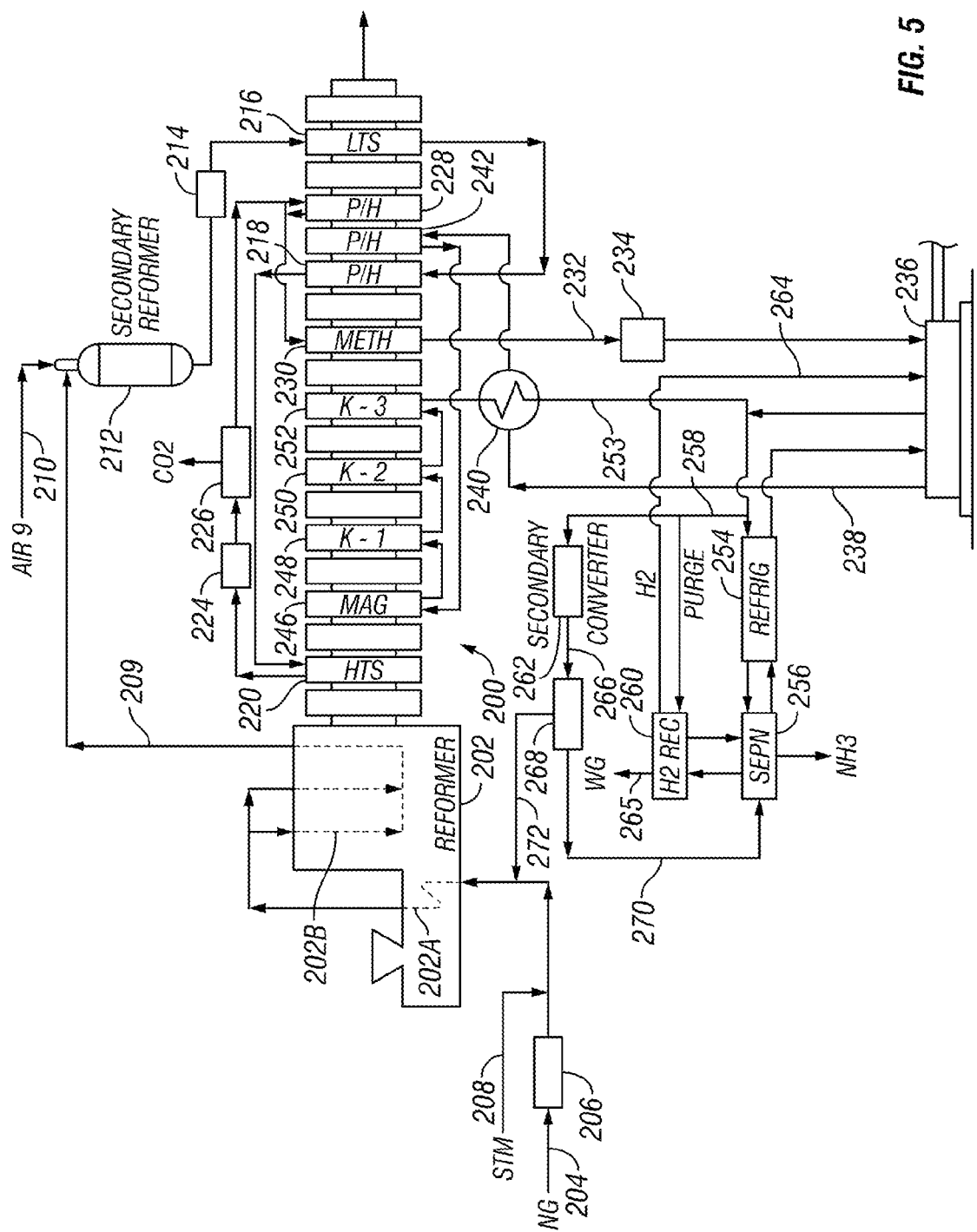
FIG. 5 is a schematic for an ammonia plant with ammonia converters cooled using flue gas from the reformer.

As seen in the embodiment of FIG. 5, both primary and secondary ammonia synthesis reactors can be disposed within the convection section of a flue gas exhaust duct 200 from the fired section of an otherwise conventional steam reformer 202. A natural gas stream 204 can be passed through sulfur removal unit 206, mixed with steam via line 208, preheated in mixed feed preheater 202A and fed to a plurality of catalyst-filled tubes 202B in the primary reformer 202. The effluent 209 can then be fed with air 210 to a conventional secondary reformer 212. The syngas can be passed through heat recovery unit 214 and low temperature shift converter 216, which can be conveniently disposed in duct 200, to convert CO and water to form additional hydrogen and CO2. Thence, the gas can be preheated in exchanger 218 and passed through high temperature shift converter 220 to form additional hydrogen, then to heat recovery unit 224, CO2 removal unit 226, preheater 228, and methanator 230 to form makeup syngas stream 232, which can be pressurized in makeup compressor 234 and fed to recycle compressor 236.

Syngas at loop pressure in line 238 can be heated in cross-exchanger 240 and preheater 242 disposed in duct 200, and fed to reactor 246 that can contain magnetite catalyst. The reactor 246 can be disposed in the duct 200 for cooling by the flue gas medium. The partially converted effluent from reactor 246 can be passed serially though reactors 248, 250, 252 containing high activity catalyst and similarly cooled by the flue gas medium in duct 200. The ammonia-rich effluent 253 can be cooled in the cross exchanger 240 and refrigeration unit 254, and ammonia can be recovered from separation unit 256, essentially as described in reference to FIG. 3 above.

A side stream 258 can be taken from line 253 and fed in part to hydrogen recovery unit 260 and in part to secondary converter 262. Hydrogen recovery unit 260 can be operated with refrigeration from the separation unit 256 essentially as described in reference to FIG. 3, and recovers a hydrogen stream 264 from the purge stream which can be recycled to the compressor 236. A waste gas stream 265 can be disposed of as discussed and described above with reference to FIG. 3. The secondary converter 262 can be a once-through ammonia converter which can be placed in a hot gas duct of a combustion unit such as package boiler unit 10 (see FIG. 1) and/or duct 200 to produce an ammonia enriched stream 266, which can be fed to ammonia stripping unit 268 to recover a concentrated ammonia stream 270 that can be processed in separation unit 256. An ammonia-lean syngas stream 272 can be recycled to the feed to the reformer 202 upstream from the mixed feed preheater 202A.

In another embodiment, systems and processes for producing one or more products from syngas are provided. A feedstock can be gasified in the presence of an oxidant to provide a syngas comprising carbon dioxide, carbon monoxide, and hydrogen. At least a portion of the syngas can be combusted to provide an exhaust gas. At least a portion of the exhaust gas can be introduced to a channel having one or more reaction zones at least partially disposed therein, wherein the one or more reaction zones are in indirect heat exchange with the exhaust gas, wherein the one or more reaction zones comprises one or more catalyst-containing tubes. A reactant can be reacted in at least one of the one or more reaction zones to provide one or more products.

Figure 6:
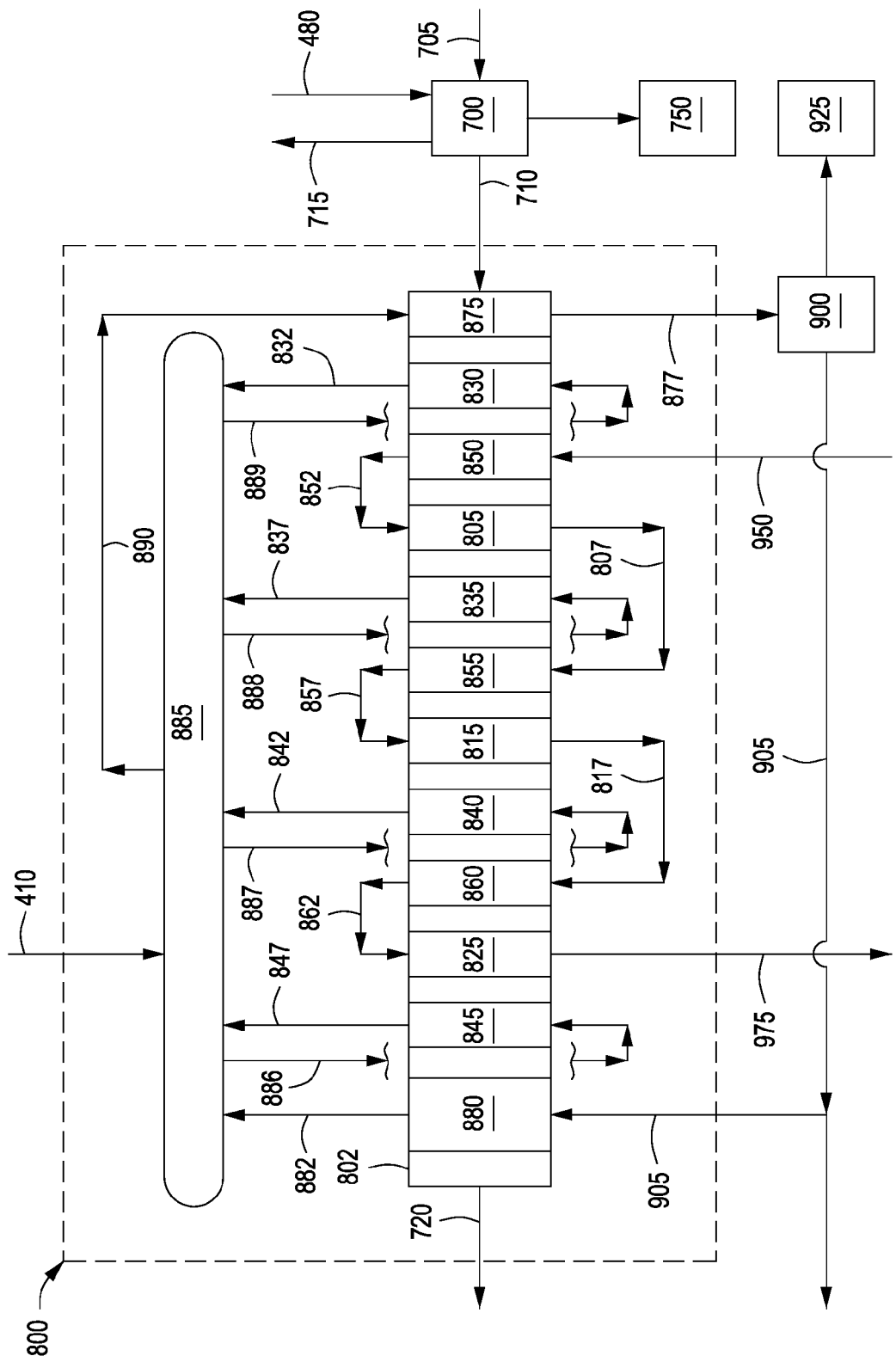
FIG. 6 depicts an illustrative system for producing one or more chemicals, according to one or more embodiments described.

FIG. 6 depicts an illustrative system for producing one or more chemicals, according to one or more embodiments. The system can include one or more hot gas ducts or channels 802, one or more reactors (three are shown 805, 815, 825), and one or more heat exchangers (nine are shown 875, 830, 850, 835, 855, 840, 860, 845, 880). The one or more reactors and the one or more heat exchangers can be at least partially disposed within the channel 802 in any order, configuration, and/or arrangement. In one or more embodiments, as depicted in FIG. 6, the channel 802 can be integrated with a heat recovery steam generation ("HRSG") unit 800. The HRSG unit 800 can include one or more steam drums or separators 885, gas and/or combustion turbines 700, steam turbines 900, and generators 750, 925.

The one or more reactors 805, 815, 825 can include one or more tubes (see FIG. 2) which can be, but are not limited to, straight tubes, U-tubes, coiled tubes, bayonet tubes, surface enhanced tubes (e.g. fins, static mixers, rifling, heat conductive packing, turbulence causing projections, or any combination thereof), and the like. One or more catalysts can be at least partially disposed within one or more of the tubes to provide one or more catalyst-containing tubes. As described and discussed above with reference to FIG. 2, the one or more reactors 805 and heat exchangers 830 can be at least partially disposed within the channel 802. The one or more catalysts can include copper, zinc, aluminum, iron, cobalt, nickel, ruthenium, rhodium, palladium, osmium, iridium, platinum, zinc, chromium, derivatives thereof, or combinations thereof.

The one or more catalysts can be disposed on one or more support materials. The catalyst support material can include, but is not limited to a refractory metal oxide, such as alumina, particularly alpha alumina, zirconia, titania, hafnia, silica, silica-alumina; rare earth modified refractory metal oxides, where the rare earth may be any rare earth metal, for example, lanthanum, yttrium; and/or alkali earth metal modified refractory metal oxides. The catalyst support material can be categorized as materials having a substantially stable surface area at reaction conditions, for example, a surface area that is not substantially altered by reaction conditions, or altered in a way that affects the reaction.

The one or more heat exchangers 875, 830, 850, 835, 855, 840, 860, 845, 880, can be any type of suitable heat exchanger design. The heat exchangers can include straight tubes, U-tubes, coiled tubes, bayonet tubes, surface enhanced tubes (e.g. fins, static mixers, rifling, heat conductive packing, turbulence causing projections, or any combination thereof), and the like.

The one or more turbines 700 can be any suitable type of turbine. For example, the turbine 700 can be a gas turbine in which a fuel can be combusted in a combustor and compressed upstream of the turbine. The compressed combusted gas can then be introduced to the gas turbine to generate power in one or more generators 750 and to provide the hot gas or exhaust gas via line 710. Another suitable type of turbine can be a combustion turbine wherein the combustion of the fuel can be integrated within the turbine (i.e. the combustion of the fuel occurs within the turbine. The fuel can be any suitable fuel, such as syngas, hydrogen, methane, other combustible fuel, or mixtures thereof. The turbine exhaust gas via line 710 can be from two or more turbines 700. The two or more turbines 700 can be the same type of turbine or different. For example, a combustion turbine and a gas turbine, two combustion turbines, or two gas turbines can be used to provide the exhaust gas via line 710.

The exhaust gas from the one or more turbines 700 can be introduced to the channel 802 via line 710. In one or more embodiments, the channel 802 can stand alone or the channel 802 can be integrated with a HRSG unit integrated with another system, such as a gasification or other syngas production process (not shown). The exhaust gas via line 710 can be a heat transfer medium which can transfer heat to or from one or more reactants or feeds introduced via line 950 to the one or more reactors 805, 815, 825 and heat exchangers ("preheaters" or "coolers") 850, 855, 860 and to or from a heat transfer medium (e.g. condensate and/or steam) introduced to the one or more heat exchangers 875, 830, 835, 840, 845, 880. The type of reaction (i.e. exothermic or endothermic) and the temperature of the reactant versus the desired reactant temperature can influence and/or determine whether heat should be transferred to or from the reactant in one of the reactors 805, 815, 825 or heat exchangers 850, 855, 860.

As shown in FIG. 6, the one or more heat exchangers (three are shown 835, 840, 845) can be alternatingly positioned with the reactors 805, 815, 825 to remove at least a portion of the heat of reaction produced (exothermic reaction) in the reactors using the exhaust gas as the heat transfer medium. In this configuration, the heat exchangers 835, 840, 845 can function as interstage coolers, cooling the exhaust gas downstream each reactor to control the temperature and conversion rates in the reactors.

In one or more embodiments, the one or more heat exchangers (three are shown 830, 835, 840) can be alternatingly positioned with the reactors 805, 815, 825 to provide at least a portion of the heat of reaction required (endothermic reaction) in the reactors using the exhaust gas as the heat transfer medium. In this configuration, the heat exchangers 830, 835, 840 can function as interstage heaters, heating the exhaust gas upstream each reactor, with the heat being indirectly transferred from the exhaust gas to the reactors.

The reactant or ("feed") via line 950 can be introduced to heat exchanger 850 to provide a preheated or cooled reactant via line 852, depending on the desired temperature of the feed and the process conditions. The preheated or cooled feed via line 852 can be introduced to the reactor 805 to provide an at least partially reacted feed via line 807. The at least partially reacted feed can be recovered as a product (not shown) via line 807 or introduced serially to subsequent heat exchangers 855, 870 and reactors 815, 825 via lines 807, 857, 817, 872, respectively, to provide one or more products via line 975. Although not shown, in one or more embodiments, any or all of the heat exchangers 850, 855, and 860 can optionally be removed or bypassed as required by the various process conditions, such temperature, heat produced, or heat required, flow rates, and exhaust gas temperature.

In one or more embodiments, the HRSG 800 can recover heat from the exhaust gas introduced via line 710 to the channel 802 and the heat generated from exothermic reactions which can occur within the one or more reactors 805, 815, 825. The recovered heat can be used to generate steam using any known steam generation system. The HRSG 800 can indirectly transfer heat from a higher temperature exhaust gas in the channel 802 to a heat transfer medium (e.g. steam and/or condensate) in heat exchangers 830, 835, 840, 845, 880, which can generate steam. The steam can be introduced to the separator 885.

In one or more embodiments, the heat transfer medium (e.g. steam and/or condensate) can be introduced via line 889 to the one or more heat exchangers or boilers 830. For example, the steam and/or condensate can be in closed loop circulation between the heat exchanger 830 and the one or more separators 885 via lines 889 and 832. The one or more steam drums 885 can separate the gas phase from the liquid phase. In one or more embodiments, the steam and/or condensate can be supplied serially from the steam drum 885 to two or more heat exchangers 830 as discussed above in reference to FIG. 1. In one or more embodiments, the steam and/or condensate can be supplied to two or more heat exchangers 830 independently. For example, steam and/or condensate can be supplied independently to two or more heat exchangers 830, 835, 840, and 845, with each heat exchanger supplied with steam and/or condensate from the separator 885 which can be heated and returned to the separator 885 independently. In this specific embodiment steam and/or condensate can be supplied to the heat exchangers 830, 835, 840, and 845 via lines 889, 888, 887, and 886 and returned to the separator 885 via lines 832, 837, 842, and 847, respectively. Although not shown, in one or more embodiments, steam and/or condensate can be supplied serially to two or more heat exchangers and then in parallel to two or more heat exchangers or any other arrangement. Various factors can determine the arrangement and/or configuration of the one or more heat exchangers, which can include, but are not limited to, desired steam temperature, the flow rates for the exhaust gas, steam/condensate and/or reactants; the exhaust gas temperature, catalyst particle size, and the amount of heat generated or required in the one or more reactors.

In one or more embodiments, steam via line 890 from the separator 885 can be superheated in heat exchanger ("superheater") 875 to any desired temperature and pressure. For example, the steam in line 877 can have a temperature of about 400° C. (750° F.) or more, 425° C. (797° F.) or more, 450° C. (842° F.) or more, 475° C. (887° F.) or more, 500° C. (932° F.) or more, or 525° C. (977° F.) or more, or 550° C. (1,022° F.) or more. The steam via line 877 can have a pressure of from about 5,600 kPa (798 psig) or more, 5,950 kPa (849 psig) or more, 6,300 kPa (899 psig) or more, 6,650 kPa (950 psig) or more, 7,000 kPa (1,001 psig) or more, 7,350 kPa (1,008 psig) or more, or 7,700 kPa (1,103 psig) or more.

At least a portion of the superheated steam via line 877 can be introduced to the one or more steam turbines 900 to drive a directly coupled electric generator 925 to generate power. In one or more embodiments, the steam via line 877 can be supplied to two or more steam turbines 900. The condensate from the one or more steam turbines 925 can be supplied to a condenser (not shown) via line 905. The condenser can provide a condensate which can be used to cool a gasification process (not shown) via line 905, and/or re-introduced to a heat exchanger ("economizer") 880 via line 905 which can be at least partially disposed within the channel 802.

The one or more feeds via line 950 can be supplied serially to the two or more reactors 805, 815, 825. Although not shown, the feed via line 950 can be supplied in parallel to the two or more reactors 805, 815, 825. Although not shown, the feed via line 950 can be supplied serially to two or more reactors which can then be mixed and supplied to one reactor or two or more reactors in parallel. Although not shown, the feed via line 950 can be supplied in parallel to two or more reactors, which can then be mixed and supplied to one or more reactors in series or in parallel if two or more reactors are desired. One or more products can be provided via line 975. Multiple, independent reactors can be installed to produce multiple products, which require different feedstocks, catalysts, and multiple product recovery lines (not shown). For example, one or more reactors can produce ammonia and one or more reactors can produce one or more Fischer-Tropsch products with each product being recovered via an independent line. In one or more embodiments, the reactors can alternate between exothermic reactions and endothermic reactions. For example, the reaction in reactor 805 can be exothermic, the reaction in reactor 815 can be endothermic, and the reaction in 825 can be exothermic.

In one or more embodiments, the feed or reactant in line 950 can contain any suitable reactants to produce one or more products. The feed can include, but is not limited to hydrogen, carbon monoxide, carbon dioxide, nitrogen, alkenes, alkanes, and aromatics. The type of products desired will determine the feed composition and ratios of the reactants introduced via line 950 to the one or more reactors 805. Typical catalytic reactions, which can be carried out in the one or more reactors 805 can include, but are not limited to, methanol synthesis, hydroformylation reactions, ammonia synthesis, the synthesis of one or more Fischer-Tropsch products, methanation, carbon dioxide shift conversion, and other processes. In one or more embodiments, the feed via line 950 can contain carbon monoxide and hydrogen or carbon monoxide, hydrogen, and carbon dioxide in desired ratios to produce methanol or Fischer-Tropsch products. In one or more embodiments, the feed can contain hydrogen and nitrogen, as discussed and described above to produce ammonia in the presence of one or more catalysts, as discussed and described above. The reactions carried out in the one or more reactors 805 can be conducted in a continuous, semi-continuous, or batch processes.

In one or more embodiments, methanol can be produced by reacting hydrogen and carbon monoxide in the presence of a catalyst in one or more methanol reactors 805. The one or more catalysts can include copper, zinc, aluminum, oxides thereof, and combinations thereof. For example, a copper-zinc oxide can be disposed on an aluminum oxide support. Methanol can be further processed to provide one or more further refined products. The one or more further refined products can include, but are not limited to, dimethyl ether (DME), formalin, acetic acid, formaldehyde, methyl-tertiary butyl ether, methylamines, methyl methacrylate, dimethyl terephthalate, methyl mercaptan, methyl chloride methyl acetate, acetic anhydride, ethylene, propylene, polyolefins, solvents, chloromethanes, glycol methyl ethers, antifreeze, fuels, aromatic hydrocarbons, derivatives thereof, mixtures thereof, or combinations thereof.

In one or more embodiments, hydroformylation reactions, which involve the addition of a —CHO group and a hydrogen atom to a carbon-carbon double bond in the presence of one or more catalysts, can provide linear and/or branched aldehydes. One or more alkenes can be converted or reacted to provide one or more aldehydes using a catalyst which can include, but is not limited to a transition metal, such as rhodium, cobalt, platinum, palladium, ruthenium, derivatives thereof, or combinations thereof. For example, the hydroformylation of propene can provide two isomeric products, butyraldehyde and isobutyraldehyde. The resulting aldehydes can be converted or reacted to provide secondary products, for example, the aldehyde can be hydrogenated to an alcohol which can be further reacted to provide esters, detergents and surfactants, solvents, lubricants, and chemical intermediates. The aldehydes can be oxidized to carboxylic acids. The alcohols and carboxylic acids can undergo esterification to provide one or more esters, which can include, but are not limited to, methyl methanoate, allyl hexanoate, ethyl formate, ethyl acetate, ethyl propionate, ethyl butyrate, ethyl pentanoate, ethyl hexanoate, benzyl acetate, methyl anthranilate, methyl benzoate, and the like.

In one or more embodiments, one or more Fischer-Tropsch products can be produced by reacting hydrogen and carbon monoxide in the presence of one or more catalysts. Illustrative Fischer-Tropsch catalysts can include, but are not limited to, cobalt, iron, palladium, rhodium, ruthenium, zinc, derivatives thereof, mixtures thereof, or combinations thereof. The Fischer-Tropsch products can include, but are not limited to, diesel fuels, kerosene, aviation fuels, naphtha, gasoline, detergents, waxes, lubricants, refinery/petrochemical feedstocks, other transportation fuels, synthetic crude oil, liquid fuels, alpha olefins, derivatives thereof, mixtures thereof, or combinations thereof.

In one or more embodiments, the methanation reaction can convert or react at least a portion of residual carbon monoxide and carbon dioxide in a hydrogen feed to methane and water to provide a hydrogen product which can be essentially free (i.e. less than 500 ppmw) of total carbon monoxide and carbon dioxide. The methanation reaction can be a catalytic process operating at a temperature sufficient for converting at least a portion of the carbon monoxide and carbon dioxide to methane and water. Suitable methanator catalysts can include, but are not limited nickel, a rare earth promoted nickel, derivatives thereof, or combinations thereof. The methanator 600 can operate at a temperature of from about 200° C. (392° F.) to about 400° C. (752° F.). The hydrogen product can contain about 50 ppm carbon monoxide and carbon dioxide or less, or 30 ppm carbon monoxide and carbon dioxide or less, or 10 ppm carbon monoxide and carbon dioxide or less. When an oxidant containing nitrogen is used the hydrogen product can contain about 20% mol dry basis to about 80% mol dry basis nitrogen.

Figure 7:
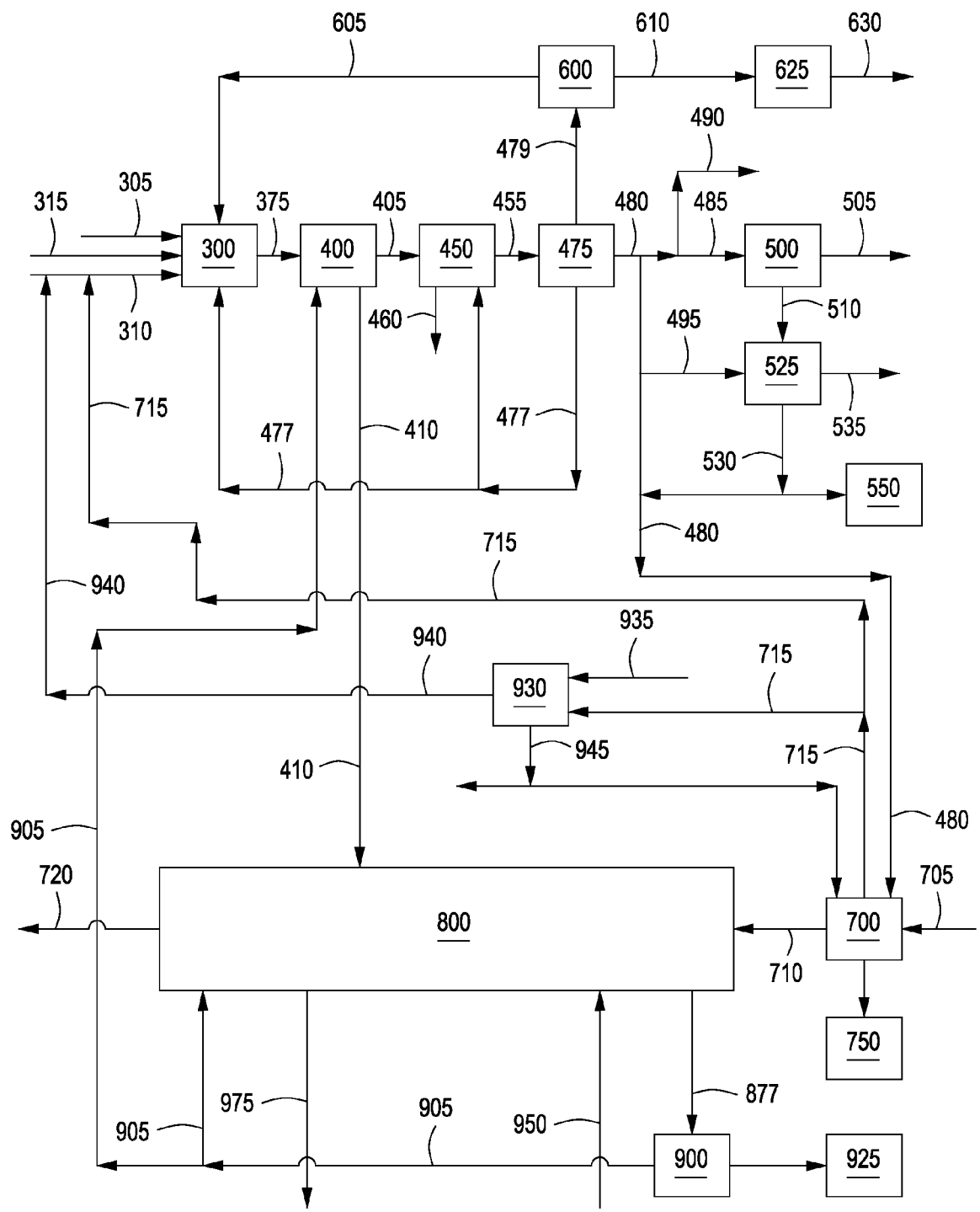
FIG. 7 depicts an illustrative syngas production and heat recovery system, according to one or more embodiments described.

FIG. 7 depicts an illustrative syngas production and heat recovery system according to one or more embodiments. Syngas can be produced using any suitable process or system. Typical syngas systems can include, but are not limited to, gasification, steam-methane reforming, autothermal reforming, partial oxidation reactions, catalytic partial oxidation reactions, and any other process that can provide a syngas, which can contain, but is not limited to hydrogen, carbon monoxide, and carbon dioxide. In one or more embodiments, two or more syngas systems can be operated in parallel or series, for example, an autothermal reformer can be used in parallel with a reforming exchanger to provide a syngas.

In one or more embodiments, the syngas system can include one or more syngas production units 300, one or more syngas coolers 400, one or more particulate removal systems 450, and one or more purification systems 475 to provide a syngas via line 480. In one or more embodiments, the gasification system can include one or more treatment systems 600, and one or more ammonia recovery systems 625. The syngas system can also include one or more reactors 500, which can convert the syngas to provide one or more Fischer-Tropsch products, methanol, ammonia, one or more hydroformylation products, other chemicals, derivatives thereof, and combinations thereof. The syngas system can further include one or more hydrogen separators 525, one or more fuel cells 550, one or more gas turbines 700, one or more HRSG units 800, one or more steam turbines 900, one or more air separation units ("ASU") 930, and/or one or more generators 750, 925 to produce fuel, power, steam, energy, and/or hydrocarbon products.

The one or more syngas production units 300 can be any suitable type of reactor. For example the one or more syngas production units can be, but are not limited to, gasifiers, autothermal reformers ("ATR"), catalytic partial oxidation ("CPOX") reactors, partial oxidation ("POX") reactors, steam-methane reformers ("SMR"), and/or reforming exchangers. The syngas production units can convert at least a portion of a feedstock in the presence of a catalyst, oxidant, heat, flame, or a combination thereof to provide a syngas which can include hydrogen, carbon monoxide, and carbon dioxide.

For simplicity and ease of description, embodiments of the syngas production reactor 300 and typical downstream processing steps will be further described in the context of a gasifier. However, the other syngas systems, e.g. ATR, CPOX, POX, SMR, and reforming exchangers are also effective and useful for generating syngas. The gasifier 300 can be any suitable type of gasifier, for example, counter-current fixed bed, co-current fixed bed, fluidized bed, and entrained flow gasifiers. Two or more gasifiers 300 can be used in the gasification system. The two or more gasifiers 300 can be the same type or different types.

In one or more embodiments, the gasification process can be any suitable gasification process, which can include, but is not limited to, gasification, combined cycle gasification, combined cycle power plant ("CCPP"), combined cycle gas turbine ("CCGT"), integrated gasification combined cycle ("IGCC"), combined gas turbine and steam turbine ("CO-GAS"), or any combination thereof.

In one or more embodiments, one or more feedstocks via line 305 and one or more oxidants via line 310 can be introduced to the one or more gasifiers 300 to produce a syngas via line 375. The type and amount of oxidant introduced to the gasifier 300 can determine the composition and physical properties of the syngas and hence, the downstream products made therefrom. The one or more oxidants via line 310 can include but are not limited to, air, excess air, oxygen, essentially oxygen, oxygen-enriched air, mixtures of oxygen and air, mixtures of oxygen and inert gas such as nitrogen and/or argon, nitrogen-free air, essentially nitrogen-free air, or combinations thereof. The oxidant can contain about 65% mol oxygen or more, or about 70% mol oxygen or more, or about 75% mol oxygen or more, or about 80% mol oxygen or more, or about 85% mol oxygen or more, or about 90% mol oxygen or more, or about 95% mol oxygen or more, or about 99% mol oxygen or more. As used herein, the term "excess air" means that the resulting molar ratio of hydrogen to nitrogen (following shift conversion) in the syngas can be less than about 3 (the typical stoichiometric ratio for ammonia syngas make-up). As used herein, the term "essentially oxygen" refers to an oxygen feed containing 51% mol oxygen or more. As used herein, the term "oxygen-enriched air" refers to air containing 21% mol oxygen or more. Oxygen-enriched air can be obtained, for example, from cryogenic distillation of air, pressure swing adsorption, membrane separation, or any combination thereof. As used herein, the term "essentially nitrogen-free," means that the oxidant in line 310 contains about 5% mol nitrogen or less, 4% mol nitrogen or less, 3% mol nitrogen or less, 2% mol nitrogen or less, or 1% mol nitrogen or less.

The one or more oxidants can be introduced via line 310 to the gasifier 300 at a rate suitable to control the temperature within the gasifier 300. The one or more oxidants in line 310 can be sub-stoichiometric air wherein the molar ratio of oxygen to carbon can be maintained at a sub-stoichiometric concentration to favor the formation of carbon monoxide over carbon dioxide in the gasifier 300. In one or more embodiments, the oxidant supplied via line 310 to the gasifier 300 can be less than five percent of the stoichiometric amount of oxygen required for complete combustion of all the carbon supplied to the gasifier 300. Excess oxygen and steam in the air can be consumed by recirculating solids, which can stabilize the temperature of the gasifier 300 during operation and periods of feed interruption if any.

In one or more embodiments, the feedstock in line 305 can include, but is not limited to, biomass (e.g., plant and/or animal matter or plant and/or animal derived matter); coal (e.g., high-sodium and low-sodium lignite, lignite, subbituminous, and/or anthracite); oil shale; coke; tar; asphaltenes; low ash or no ash polymers; hydrocarbon-based polymeric materials; biomass derived material; or by-product derived from manufacturing operations. The hydrocarbon-based polymeric materials can include, for example, thermoplastics, elastomers, rubbers, including polypropylenes, polyethylenes, polystyrenes, including other polyolefins, homo polymers, copolymers, block copolymers, and blends thereof, PET (polyethylene terephthalate), poly blends, other polyolefins, poly-hydrocarbons containing oxygen, heavy hydrocarbon sludge and bottoms products from petroleum refineries and petrochemical plants such as hydrocarbon waxes, blends thereof, derivatives thereof, and combinations thereof.

The feedstock can include a mixture or combination of two or more carbonaceous materials. For example, the feedstock can include a mixture or combination of two or more low ash or no ash polymers, biomass derived materials, or by-products derived from manufacturing operations. The feedstock can include one or more carbonaceous materials combined with one or more discarded consumer products, such as carpet and/or plastic automotive parts/components including bumpers and dashboards. Such discarded consumer products are preferably suitably reduced in size to fit within the gasifier 300. The feedstock can include one or more recycled plastics such as polypropylene, polyethylene, polystyrene, derivatives thereof, blends thereof, or any combination thereof. Accordingly, the process can be useful for accommodating mandates for proper disposal of previously manufactured materials.

In one or more embodiments, the feedstock via line 300 can be conveyed to the gasifier 300 within the carrier fluid as a slurry or suspension. In one or more embodiments, the feedstock can be dried, for example to 18% moisture, and then pulverized by milling units such as one or more parallel bowl mills prior to feeding to the gasifier 300. For example, the feedstock can be reduced to an average particle diameter size of from about 50 μm to about 500 μm; about 50 μm to about 400 μm; about 150 μm to about 450 μm; or about 250 μm to about 400 μm. In one or more embodiments, a carrier fluid (not shown) can be added to the feedstock in line 305 either before or after reducing the feedstock particle size.

In one or more embodiments, one or more oxygen scavengers and/or sorbents can be added to the feedstock in line 305 (not shown) or the gasifier 300 to limit the oxygen concentration to levels below the threshold required to support uncontrolled reactions with hydrogen. The oxygen scavenger can include an ash containing reactive carbon which, by reacting to form carbon monoxide and/or carbon dioxide, can chemically bond with residual oxygen present in the gasifier 300. In one or more embodiments, the sorbents can be used to dust or coat the feedstock prior to introduction to the gasifier 300 to reduce agglomeration of the feedstock within line 305 and within the gasifier 300. In one or more embodiments, the sorbents can be ground to an average particle size of about 5 μm to about 100 μm, or about 10 μm to about 75 μm prior to mixing with the feedstock in line 305 or introduction directly to the gasifier 300. Illustrative sorbents can include, but are not limited to, carbon rich ash, limestone, dolomite, and coke breeze. Residual sulfur released from the feedstock can be captured by native calcium in the feed or by a calcium-based sorbent to form calcium sulfide.

The syngas can exit the one or more gasifiers 300 via line 375. The syngas in line 375 can contain 80% mol or more carbon monoxide and hydrogen, 85% mol or more carbon monoxide and hydrogen, about 90% mol or more carbon monoxide and hydrogen, about 95% mol or more carbon monoxide and hydrogen. In one or more embodiments, the syngas in line 375 can contain 75% mol or more carbon monoxide and hydrogen with the balance being primarily carbon dioxide and methane. In one or more embodiments, the carbon monoxide content of the syngas in line 375 can range from a low of about 10% mol, 20% mol, or 30% mol to a high of about 50% mol, 70% mol or 85% mol or more. In one or more embodiments, the hydrogen content of the syngas can range from a low of about 1% mol, 5% mol, or 10% mol to a high of about 30% mol, 40% mol or 50% mol or more. In one or more embodiments, the hydrogen content of the raw syngas can range from about 20% mol to about 30% mol or more.

In one or more embodiments, the carbon dioxide concentration in the syngas in line 375 can be about 25% mol or less, 20% mol or less, 15% mol or less, 10% mol or less, 5% mol or less, 3% mol or less, 2% mol or less, or 1% mol or less. In one or more embodiments, the methane concentration in the syngas in line 375 can be about 15% mol or less, 10% mol or less, 5% mol or less, 3% mol or less, 2% mol or less, or 1% mol or less. In one or more embodiments, the water concentration in the syngas in line 375 can be about 40% mol or less, 30% mol or less, 25% mol or less, 20% mol or less, 15% mol or less, 10% mol or less, 5% mol or less, 3% mol or less, 2% mol or less, or 1% mol or less. In one or more embodiments, the syngas in line 375 can be nitrogen-free or essentially nitrogen-free, e.g. containing less than 0.5% mol nitrogen. In one or more embodiments, the syngas in line 375 can contain less than 25 mol %; less than 20 mol %; less than 15 mol %; less than 10 mol %; or less than 5% mol of combined nitrogen, methane, carbon dioxide, water, hydrogen sulfide, and hydrogen chloride.

In one or more embodiments, the heating value of the syngas in line 375, corrected for heat losses and dilution effects, can range from about 1,850 kJ/m$^3$ (50 Btu/scf) to about 2,800 kJ/m$^3$ (75 Btu/scf); about 1,850 kJ/m$^3$ (50 Btu/scf) to about 3,730 kJ/m$^3$ (100 Btu/scf); about 1,850 kJ/m$^3$ (50 Btu/scf) to about 4,100 kJ/m$^3$ (110 Btu/scf); about 1,850 kJ/m$^3$ (50 Btu/scf) to about 5,200 kJ/m$^3$ (140 Btu/scf); about 1,850 kJ/m$^3$ (50 Btu/scf) to about 6,700 kJ/$^3$ (180 Btu/scf); about 1,850 kJ/m$^3$ (50 Btu/scf) to about 7,450 kJ/m$^3$ (200 Btu/scf); about 1,850 kJ/m$^3$ (50 Btu/scf) to about 9,300 kJ/m$^3$ (250 Btu/scf); or about 1,850 kJ/m$^3$ (50 Btu/scf) to about 10,250 kJ/m$^3$ (275 Btu/scf).

The syngas via line 375 can exit the gasifier 300 at a temperature ranging from about 575° C. (1,067° F.) to about 1,650° C. (3,002° F.). In one or more embodiments, the syngas in line 375 can be supplied to a syngas cooler 400, which can provide a cooled syngas via line 405. The cooled syngas can exit the syngas cooler 400 at a temperature of about 475° C. (887° F.) or less, 425° C. (797° F.) or less, 375° C. (707° F.) or less, 325° C. (617° F.) or less, 250° C. (482° F.) or less, 200° C. (392° F.) or less, 150° C. (302° F.) or less, or 100° C. (212° F.) or less.

The syngas can be cooled using a heat transfer medium introduced to the syngas cooler 400 via line 905. The heat transfer medium can be process water, boiler feed water, or the like. Heat from the syngas can be indirectly transferred to the heat transfer medium to provide steam which can be recovered via line 410. The steam via line 410 can be introduced to the HRSG unit 800.

The one or more particulate removal systems 450 can be used to partially or completely remove particulates from the cooled syngas in line 405 to provide separated particulates via line 460 and a separated syngas via line 455. In one or more embodiments, the one or more particulate removal systems 450 can be used to partially or completely remove particulates from the syngas in line 375 before cooling (not shown). For example, the syngas via line 375 can be introduced directly to the particulate removal system 450, resulting in hot gas particulate removal (e.g. from about 550° C. (1,022° F.) to about 1,050° C. (1,922° F.)). Although not shown, in one or more embodiments, two particulate removal systems 450 can be used, for example one particulate removal system 450 can be upstream of the cooler 400 and one particulate removal system 450 can be downstream of the syngas cooler 400.

The one or more particulate removal systems 300 can include one or more separation devices such as conventional disengagers and/or cyclones (not shown). Particulate control devices ("PCD") capable of providing an outlet particulate concentration below the detectable limit of about 0.1 ppmw can also be used. Illustrative PCDs can include but are not limited to, sintered metal filters, metal filter candles, and/or ceramic filter candles (for example, iron aluminide filter material).

The solid particulates via line 460 can be purged from the system or recycled to the gasifier 300 (not shown). Although not shown, the temperature of the separated syngas in line 455 can be further reduced using one or more coolers ("secondary coolers"). The temperature of the separated syngas in line 455 can be at a temperature of about 475° C. (887° F.) or less, 425° C. (797° F.) or less, 375° C. (707° F.) or less, 325° C. (617° F.) or less, 250° C. (482° F.) or less, 200° C. (392° F.) or less, 150° C. (302° F.) or less, or 100° C. (212° F.) or less.

The separated syngas in line 455 can be treated within one or more purification systems 475 to remove contaminants and provide a waste via line 479, and a treated syngas via line 480. The one or more purification systems 475 can include units, processes, or devices to remove sulfur, sulfur containing compounds, acid gases, mercaptans, hydrogen cyanide, metal carbonyls, and other contaminating compounds from the separated syngas in line 455. Illustrative catalytic purification systems 475 can include, but are not limited to, units using zinc titanate, zinc ferrite, tin oxide, zinc oxide, iron oxide, copper oxide, cerium oxide, or mixtures thereof. Illustrative process-based purification systems 475 can include, but are not limited to, the Selexol™ process, the Rectisol® process, the CrystaSulf® process, and the Sulfinol® Gas Treatment Process.

One or more amine solvents such as methyl-diethanolamine ("MDEA") can be used in the one or more purification systems to remove acid gas from the syngas in line 455. Physical solvents such as Selexol™ (dimethyl ethers of polyethylene glycol) or Rectisol® (cold methanol), can also be used. If the syngas in line 455 contains carbonyl sulfide, the carbonyl sulfide can be converted by hydrolysis to hydrogen sulfide by reaction with water over a catalyst and then absorbed using the methods described above. If the syngas in line 390 contains mercury, the mercury can be removed using a bed of sulfur-impregnated activated carbon.

A cobalt-molybdenum catalyst can be incorporated into the one or more purification systems 475 to perform a sour shift conversion of the syngas. The Co—Mo catalyst can operate at a temperature of about 290° C. (554° F.) in presence of hydrogen sulfide, such as about 100 ppmw hydrogen sulfide. If Co—Mo catalyst is used to perform a sour shift, subsequent downstream removal of sulfur can be accomplished using any of the above described sulfur removal process and/or techniques.

The waste or (sour water) via line 479 can be introduced to one or more treatment systems 600 via line 479. The treatment systems 600 can include a filter to remove particulates, activated carbon to remove heavy metals and organic material, a degassing drum, hydrogen sulfide strippers, and stripped-water recuperators (not shown). Gaseous contaminants, such as hydrogen sulfide, hydrogen cyanide, and carbon dioxide can be released during the treatment process. The contaminants can be recycled to the oxidation zone of the gasifier 300 via line 605 where the contaminants can be destroyed. Water from the hydrogen sulfide stripper can be introduced via line 610 to an ammonia recovery system 625 which can produce a concentrated ammonia solution via line 630. The ammonia in line 630 can be used in a selective catalytic reduction (SCR) unit (not shown) which can reduce nitrogen oxides emissions from the process, sold, or used to produce other chemicals, such as urea.

In one or more embodiments, at least a portion of the syngas from the one or more syngas purification systems 475 can be introduced via line 477 to the gasifier 300. At least a portion of the syngas from the one or more syngas purification systems 475 can be introduced via line 477 to the particulate removal system 450. The syngas recycled to the gasifier 300 can first undergo syngas purification, or it can be introduced to the gasifier 300 before the syngas treatment steps via line 455 (not shown). The recycled syngas via line 477 to the gasifier 300 can be used as a fuel in the gasifier 300. The syngas can be compressed in a compressor (not shown) prior to introducing at least a portion of the syngas in line 477 to the gasifier 300, feed in line 305, particulate removal system 450, or a combination thereof.

In one or more embodiments, at least a portion of the treated syngas via line 480 can be combusted to produce or generate power (e.g. electricity) in the one or more turbines 700. In one or more embodiments, at least a portion of the treated syngas in line 480 can be recovered via line 490 and sold as a commodity. In one or more embodiments, at least a portion of the treated syngas in line 480 can be supplied to one or more reactors 500 via line 485 to produce one or more Fischer-Tropsch products, ammonia, methanol, other chemicals, derivatives thereof, and/or combinations thereof. The reactors 500 can produce the same or different products as the one or more reactors 805 that are at least partially disposed within the channel 802 of the HRSG unit 800 (see FIG. 6). In one or more embodiments, at least a portion of the treated syngas via line 480 and/or the converted gas from the gas converter 500 via line 510 can be introduced to one or more hydrogen separators 525 via line 495 to provide a hydrogen rich effluent via line 530 which can be used in hydrogenation processes, fuel cell energy processes, ammonia production, as a fuel, or other useful applications.

In one or more embodiments, the one or more reactors 500 can be used to convert the treated syngas in line 485 to provide a shift converted syngas which can have increased carbon dioxide content. At least one of the one or more reactors 500 can include one or more shift converters to adjust the hydrogen to carbon monoxide ratio ($H_2$:CO) of the syngas by converting carbon monoxide to carbon dioxide. Within the one or more shift converters, a water-gas shift reaction can react at least a portion of the carbon monoxide in the treated syngas introduced via line 485 with water in the presence of a catalyst and/or high temperature to produce hydrogen and carbon dioxide. The one or more shift reactors can include, but are not limited to, single stage adiabatic fixed bed reactors; multiple-stage adiabatic fixed bed reactors with interstage cooling, steam generation or cold quench reactors; tubular fixed bed reactors with steam generation or cooling; fluidized bed reactors, or any combination thereof. For example, a sorption enhanced water-gas shift ("SEWGS") process, utilizing a pressure swing adsorption unit having multiple fixed bed reactors packed with shift catalyst and high temperature (around 475° C. (887° F.)) carbon dioxide adsorbent, can be used.

In one or more embodiments, the shift converters can include two reactors arranged in series. A first shift converter (high temperature shift converter) can be operated at a temperature of from about 350° C. (662° F.) to about 400° C. (752° F.) to convert a majority of the carbon monoxide present in the treated syngas introduced via line 485 to carbon dioxide using a catalyst which can be, but is not limited to iron oxide, zinc ferrite, magnetite, chromium oxides, derivatives thereof, or any combination thereof. A second shift converter (low temperature shift converter) can be operated at a temperature of about 150° C. (302° F.) to about 200° C. (392° F.) to further convert at least a portion of remaining carbon monoxide to carbon dioxide using a catalyst which can be, but is not limited to copper, zinc, copper promoted chromium, derivatives thereof, or any combination thereof. In one or more embodiments, a third shift converter (medium temperature shift converter) operating at a temperature between the relatively high and low shift converters can be used in combination with or in place of one or both of the relatively high and low temperature shift converters. The medium temperature shift converter can use a catalyst that can include, but is not limited to, iron oxide, chromium oxide, derivatives thereof, or any combination thereof. The medium temperature shift converter can be operated at a temperature of from about 250° C. (482° F.) to about 300° C. (572° F.).

In one or more embodiments, at least a portion of the treated syngas and/or the shift converted syngas can be introduced into one or more carbon dioxide recovery units which can be integrated with the one or more gas converters to provide a syngas having reduced carbon dioxide content ("carbon dioxide lean syngas"). In one or more embodiments, the carbon dioxide recovery unit can use propylene carbonate, other alkyl carbonates, dimethyl ethers of polyethylene glycol of two to twelve glycol units (Selexol™ process), n-methyl-pyrrolidone, sulfolane, the Sulfinol® Gas Treatment Process, monoethanolamine ("MEA"), diethanolamine ("DEA"), triethanolamie ("TEA"), potassium carbonate, methyldiethanolamine ("MDEA"), diglycolamine ("DGA"), diisopropanolamine ("DIPA"), hydrophobic zeolites, derivatives thereof, mixtures thereof, or any combination thereof.

The recovered carbon dioxide can be used in a fuel recovery process to enhance the recovery of oil and gas. In an illustrative oil recovery process, carbon dioxide can be injected and flushed into an area beneath an existing well where "stranded" oil exists. The water and carbon dioxide removed with the crude oil can then be separated and recycled.

In one or more embodiments, at least one of the one or more reactors 500 can be used to produce one or more Fischer-Tropsch products, which can include, but are not limited to, diesel fuels, kerosene, aviation fuels, naphtha, gasoline, detergents, waxes, lubricants, refinery/petrochemical feedstocks, other transportation fuels, synthetic crude oil, liquid fuels, alpha olefins, derivatives thereof, mixtures thereof, or combinations thereof. The reaction can be carried out in any type of reactor, e.g., fixed bed, moving bed, fluidized bed, slurry, bubbling bed, etc. using copper, ruthenium, iron or cobalt based catalysts, or combinations thereof, under conditions ranging from about 190° C. (374° F.) to about 450° C. (842° F.) depending on the reactor configuration. Additional reaction and catalyst details can be found in U.S. Patent Application No. 20050284797 and U.S. Pat. Nos. 5,621,155; 6,682,711; 6,331,575; 6,313,062; 6,284,807; 6,136,868; 4,568,663; 4,663,305; 5,348,982; 6,319,960; 6,124,367; 6,087,405; 5,945,459; 4,992,406; 6,117,814; 5,545,674 and 6,300,268.

The Fischer-Tropsch products can be liquids suitable for upgrading to a variety of products. Certain products, e.g. $C_4$-$C_5$ hydrocarbons, can be high quality paraffin solvents which, if desired, can be hydrotreated to remove olefin impurities, or employed without hydrotreating to produce a wide variety of wax products. Hydrocarbons, including $C_{16}$ and higher compounds can be upgraded by various hydroconversion reactions, e.g., hydrocracking, hydroisomerization catalytic dewaxing, isodewaxing, etc. or combinations thereof, to produce mid-distillates, diesel fuels, jet fuels, isoparaffinic solvents, lubricants, drilling oils suitable for use in drilling muds, technical and medicinal grade white oil, chemical materials, and various specialty products In one or more embodiments, at least one of the one or more reactors 500 can include one or more slurry bubble column reactors to produce one or more Fischer-Tropsch products. The slurry bubble column reactors can operate at a temperature of less than 225° C. (437° F.) and under a vacuum to about 4,140 kPa (586 psig), or about 1,720 kPa (235 psig) to about 2,410 kPa (335 psig) which can use, for example, a cobalt catalyst promoted with rhenium supported on titania having a Re:Co weight ratio in the range of about 0.01 to about 1 and containing from about 2% by weight to about 50% by weight cobalt. The catalyst within the slurry bubble column reactors can include, but is not limited to, a titania support impregnated with a salt of a catalytic copper or an Iron Group metal, a polyol or polyhydric alcohol and, optionally, a rhenium compound or salt. Examples of polyols or polyhydric alcohols include glycol, glycerol, derythritol, threitol, ribitol arabinitol, xylitol, allitol, dulcitol, gluciotol, sorbitol, and mannitol. The catalytic metal, copper or Iron Group metal as a concentrated aqueous salt solution, for example cobalt nitrate or cobalt acetate, can be combined with the polyol and optionally perrhenic acid while adjusting the amount of water to obtain 15% by weight cobalt in the solution and using optionally incipient wetness techniques to impregnate the catalyst onto rutile or anatase titania support, optionally spray-dried and calcined. This method reduces the need for rhenium promoter. Additional details can be found in U.S. Pat. Nos. 5,075,269 and 6,331,575.

In one or more embodiments, at least one of the one or more reactors 500 can be used to produce methanol, alkyl formates, dimethyl ether, ammonia, acetic anhydride, acetic acid, methyl acetate, acetate esters, vinyl acetate and polymers, ketenes, formaldehyde, dimethyl ether, olefins, urea, derivatives thereof, and/or combinations thereof. For methanol production, for example, the Liquid Phase Methanol Process can be used. In this process, the carbon monoxide in the syngas in line 485 can be directly converted into methanol using a slurry bubble column reactor and catalyst in an inert hydrocarbon oil reaction medium which can conserve heat of reaction while idling during off-peak periods for a substantial amount of time while maintaining good catalyst activity. Additional details can be found in U.S. patent application Ser. No. 11/311,766 and prior published Heydorn, E. C., Street, B. T., and Kornosky, R. M., "Liquid Phase Methanol (LPMEOH™) Project Operational Experience," (Presented at the Gasification Technology Council Meeting in San Francisco on Oct. 4-7, 1998). Gas phase processes for producing methanol can also be used. For example, known processes using copper based catalysts, the Imperial Chemical Industries process, the Lurgi process and the Mitsubishi process can be used.

In one or more embodiments, for ammonia production, at least one of the one or more reactors 500 can be adapted to operate the Haber-Bosch process. In one or more embodiments, for alkyl formate production, such as for example, methyl formate, any of several processes wherein carbon monoxide and methanol are reacted in either the liquid or gaseous phase in the presence of an alkaline catalyst or alkali or alkaline earth metal methoxide catalyst can be used. Additional details can be found in U.S. Pat. Nos. 3,716,619; 3,816, 513; and 4,216,339.

Although not shown, in one or more embodiments, at least a portion of the converted syngas via line 510 can be sold or upgraded using further downstream processes. In one or more embodiments, at least a portion of the converted syngas via line 510 can be directed to the one or more hydrogen separators 525. In one or more embodiments, at least a portion of the treated syngas in line 480 can bypass the one or more reactors 500 described above, and can be fed directly to the one or more hydrogen separators 525 via line 495.

The one or more hydrogen separators 525 can include any system or device capable of selectively separating hydrogen from syngas to provide one or more purified hydrogen products via line 530 and one or more waste products via line 535.

For example, the hydrogen separators 525 can utilize pressure swing absorption, cryogenic distillation, and/or semi-permeable membranes. Suitable absorbents can include caustic soda, potassium carbonate or other inorganic bases, and/or alanolamines. In one or more embodiments, at least a portion of the hydrogen product via line 530 can be used as a feedstock to one or more fuel cells 550. In one or more embodiments, at least a portion of the hydrogen product via line 535 can be combined with the treated syngas in line 480 prior to use as a fuel in the one or more turbines 700.

In one or more embodiments, as discussed above, at least a portion of the treated syngas via line 480 can be combusted in one or more combustors (not shown) and/or the one or more turbines 700 to provide the exhaust gas via line 710. Air or other suitable oxidant via line 705 can be introduced to the one or more combustors and/or the one or more turbines 700. In one or more embodiments, the exhaust gas via line 710 can be introduced to one or more HRSG units 800 to provide steam via line 820, and the heat transfer medium for the one or more reactors, pre-heaters/pre-coolers, and heat exchangers which can be at least partially disposed within the HRSG unit 800, as discussed and described above with reference to FIG. 6.

In one or more embodiments, oxygen, oxygen-enriched air, or essentially oxygen via line 940 from the ASU 930 can be introduced to the gasifier 300. The ASU 930 can provide a nitrogen-lean and oxygen-rich feed to the one or more gasifiers 300, thereby minimizing the nitrogen concentration in the syngas provided via line 375. For example, in one or more embodiments, the syngas via line 375 can be essentially nitrogen-free, e.g. containing less than 0.5% nitrogen/argon. The ASU 930 can be a high-pressure, cryogenic type separator. The ASU 930 can provide a portion or all of the oxidant introduced to the gasifier 300. For example, the ASU 930 can provide from about 10%, about 30%, about 50%, about 70%, about 90%, or about 100% of the total oxidant fed to the gasifier 300.

Ambient air or other suitable oxidant via line 705 can be compressed by the turbine 700 to provide compressed air via line 715 which can be introduced to the gasifier 300 and/or ASU 930. Ambient air can be compressed in the turbine 700 to provide compressed air via line 715. Nitrogen separated in the ASU 930 can be purged and/or introduced to the one or more turbines 700 via line 945 to reduce nitrogen oxides emissions by lowering the combustion temperature in the combustor or combustion turbine 700. The nitrogen acts as a diluent with no heating value, i.e. a heat sink. To further minimize nitrogen oxides formation, the syngas via line 480 introduced to the one or more turbine 700 can be saturated with water (not shown).

Figure 8:
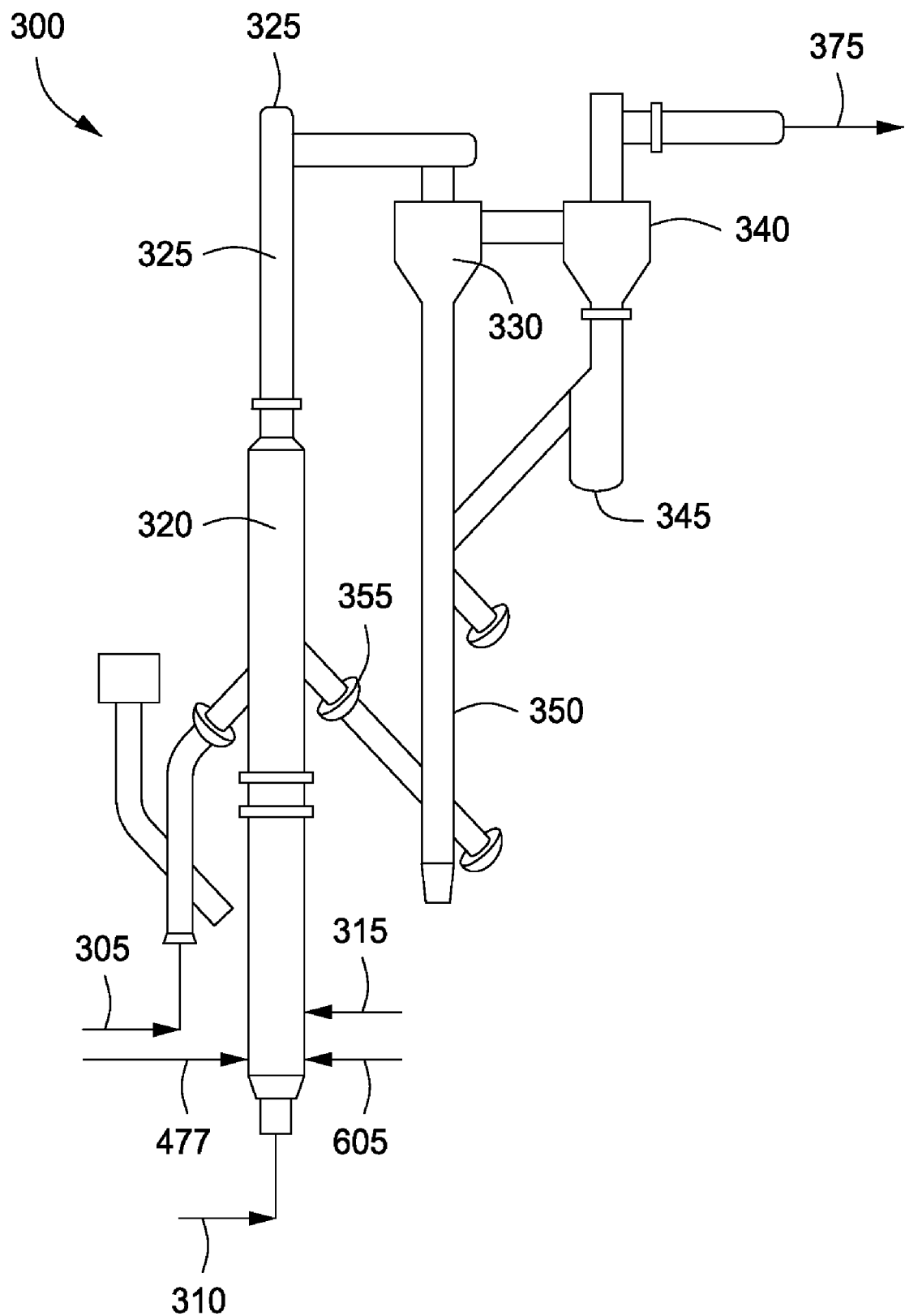
FIG. 8 depicts an illustrative gasifier according to one or more embodiments described.

FIG. 8 depicts an illustrative gasifier 300, according to one or more embodiments. The gasifier 300 can include a single reactor train or two or more reactor trains arranged in series or parallel. Each reactor train can include one or more mixing zones 320, risers 325, and disengagers 330, 340. Each reactor train can be configured independent from the others or configured where any of the one or more mixing zones 320, risers 325, disengagers 330, 340 can be shared. For simplicity and ease of description, embodiments of the gasifier 300 will be further described in the context of a single reactor train as depicted in FIG. 8.

The one or more feedstocks via line 305 and one or more oxidants via line 310 can be combined in the mixing zone 320 to provide a gas mixture. In one or more embodiments, steam via line 315, the syngas from the one or more syngas purification systems via line 477, and the contaminants via line 605 from the one or more treatment systems can be introduced to the mixing zone 320. In one or more embodiments, the feedstock and oxidant can be introduced separately, as shown, to the mixing zone 320 or mixed prior to introduction to the mixing zone (not shown). In one or more embodiments, the feedstock and oxidant can be introduced sequentially or simultaneously to the gasifier 300. The introduction of the feedstock, oxidant, and/or steam to the gasifier 300 can be continuous or intermittent depending on desired product types and grades. The one or more oxidants can be introduced at the bottom of the mixing zone 320 to increase the temperature within the mixing zone 320 and riser 325 by combusting any carbon contained within the recirculated particulates (not shown) to form an ash ("char").

The gasifier 300 can be operated at a temperature sufficient to not melt the ash, such as from about 275° C. (527° F.) to about 1,700° C. (3,092° F.), or from about 550° C. (1,022° F.) to about 1,050° C. (1,922° F.), or from about 275° C. (527° F.) to about 950° C. (1,742° F.). Heat can be supplied by burning the carbon in the recirculated solids in the lower part of the mixing zone 320 before recirculated solids contact the entering feedstock. Startup can be initiated by bringing the mixing zone 320 to a temperature from about 500° C. (932° F.) to about 650° C. (1,202° F.) and optionally by feeding coke breeze or the equivalent to the mixing zone 320 to further increase the temperature of the mixing zone 320 to about 900° C. (1,652° F.).

The operating temperature of the gasifier 300 can be controlled by the recirculation rate and residence time of the solids within the riser 325; by reducing the temperature of the ash prior to recycle (not shown) to the mixing zone 320; by the addition of steam via line 315 to the mixing zone 320; and/or by the addition of oxidant via line 310 to the mixing zone 320. The recirculating solids also can serve to rapidly heat the incoming feedstock which also minimizes tar formation.

The residence time and temperature in the mixing zone 320 and the riser 325 can be sufficient for water-gas shift reaction to reach equilibrium. The residence time of the feedstock in the mixing zone 320 can be greater than about 2 seconds. The residence time of the feedstock in the mixing zone 320 can be greater than about 5 seconds. The residence time of the feedstock in the mixing zone 320 can be greater than about 10 seconds.

The mixing zone 320 can be operated at pressures of from about 100 kPa (0 psig) to about 4,600 kPa (653 psig) to increase thermal output per unit reactor cross-sectional area and enhance energy output in any subsequent power cycle. The mixing zone 320 can be operated at pressures from about 650 kPa (80 psig) to about 2,550 kPa (355 psig). The mixing zone 320 can be operated at pressures from about 650 kPa (80 psig) to about 3,200 kPa (450 psig). The mixing zone 320 can be operated at pressures from about 650 kPa (80 psig) to about 3,950 kPa (559 psig).

The operating temperature of the mixing zone 320 can range from about 250° C. (482° F.), 400° C. (752° F.) or 550° C. (1,022° F.) to about 650° C. (1,202° F.), 825° C. (1,517° F.), or 1,000° C. (1,832° F.). The operating temperature of the mixing zone 320 can range from about 350° C. (662° F.) to about 950° C. (1,742° F.), about 475° C. (887° F.) to about 900° C. (1,652° F.), or about 650° C. (1,202° F.) to about 875° C. (1,607° F.).

The gas mixture can flow through the mixing zone 320 into the riser 325 where additional residence time allows the char gasification, steam/methane reforming, tar cracking, and/or water-gas shift reactions to occur. The riser 325 can operate at a higher temperature than the mixing zone 320, and can have a smaller diameter than the mixing zone 320. The superficial gas velocity in the riser 325 can range from about 3 m/s (10 ft/s) to about 27 m/s (90 ft/s), or from about 6 m/s (20 ft/s) to about 24 m/s (80 ft/s), or from about 9 m/s (30 ft/s) to about 21 m/s (70 ft/s), or from about 9 m/s (30 ft/s) to about 12 m/s (40 ft/s), or from about 11 m/s (35 ft/s) to about 18 m/s (60 ft/s). Suitable temperatures in the riser 325 can range from about 320° C. (608° F.) to about 1,100° C. (2,012° F.).

The gas mixture can exit the riser 325 and enter the disengagers 330, 340 where the larger particulates can be separated from the gas and recycled back to the mixing zone 320 via one or more conduits, including, but not limited to, a standpipe 350, and/or j-leg 355. The j-leg 355 can include a non-mechanical "j-valve" to increase the effective solids residence time, increase the carbon conversion, and minimize aeration requirements for recycling solids to the mixing zone 320. The disengagers 330, 340 can be cyclones. One or more particulate transfer devices 345, such as one or more loop seals, can be located downstream of the disengagers 330, 340 to collect separated particulates. Any entrained or residual particulates in the syngas stream 375 can be removed using the one or more particulate removal systems 300 (shown in FIG. 7).

The average particle diameter size of the feedstock can be used as a control variable to optimize particulate density of the solids recycled to the mixing zone via the standpipe 350. The feedstock particle size can be varied to optimize the particulate mass circulation rate, and to improve the flow characteristics of the gas mixture within the mixing zone 320 and riser 325.

Steam via line 315 can be supplied to the gasifier 300 to control the hydrogen to carbon monoxide ratio ($H_2$:CO) within the gasifier 300. Since the outlet temperature of the gasifier 300 can be proportionately less than comparable gasifiers (i.e. slag type), the amount of thermal heat versus chemical heat in the syngas can be comparably less in the gasifier 300. Therefore, steam can be used to adjust by shift the $H_2$:CO ratio with a smaller energy penalty than other entrained flow gasifiers operating at higher temperatures. Because of the reduced operating temperature within the gasifier (i.e. less than 1,600° C. (2,912° F.)), less energy is consumed to control and optimize the $H_2$:CO ratio, thus the production of hydrogen can be increased without a commensurate increase in steam demand within the gasifier 300. For example, the syngas leaving the gasifier 300 can have a $H_2$:CO of at least 0.2. In one or more embodiments, the $H_2$:CO ratio can be at least 0.5. The $H_2$:CO ratio can be about 0.25 to about 2.5. The $H_2$:CO ratio can be about 0.4 to about 2.0. The $H_2$:CO ratio can be about 0.5 to about 1.5. The $H_2$:CO ratio can be about 0.8 to about 1.0.

EXAMPLES

The foregoing discussion can be further described with reference to the following non-limiting examples.

Example 1

Table 1 below provides exemplary tube specifications for the embodiment of the heat transfer units in FIGS. 1 and 2, including the synthesis reactors 22, 24, the BFW heating units 30, 32, 34, and the syngas preheater unit 14. Typically, the inner diameter of catalyst-containing tubes 23 can range from about 7.5 cm to about 10.0 cm, while the outer diameter desirably ranges from about 8.25 cm to about 10.8 cm. The length of the catalyst tubes 23 typically ranges from about 5.0 m to about 8.0 m, depending upon the diameter or other transverse dimension of the exhaust duct 16.

The transverse orientation of the reactor tubes 23 and a relatively high exhaust gas velocity through the exhaust duct 16 may provide a suitably high convective heat transfer coefficient to allow the reactors 22, 24 to use less costly smooth-walled reactor tubes 23. Alternatively, as listed in Table 1, the reactor tubes 23 can use extended surfaces such as fins to enhance heat transfer.

TABLE 1

Heat Transfer Coil Information

|  | Preheat | BFW 1 | Reactor 1 | BFW 2 | Reactor 2 | BFW 3 |
|---|---|---|---|---|---|---|
| Element ID | 14 | 34 | 22 | 32 | 24 | 30 |
| Coil Material | S/S 304 H | Carbon Steel | S/S 304 H | Carbon Steel | S/S 304 H | Carbon Steel |
| Tube OD (cm) | 8.89 | 5.08 | 8.89 | 5.08 | 8.89 | 5.08 |
| Min. Wall (cm) | 0.665 | 0.318 | 0.665 | 0.318 | 0.665 | 0.318 |
| Tubes per Row | 11 | 16 | 11 | 16 | 11 | 16 |
| Tube Rows | 4 | 2 | 12 | 1 | 12 | 12 |
| Passes | 11 | 16 | 132 | 16 | 132 | 16 |
| Spacing, Centers × Rows (cm) | 6.5 × 5.63 | 4.5 × 3.9 | 6.5 × 5.63 | 4.5 × 3.9 | 6.5 × 5.63 | 4.5 × 3.9 |
| Fin Material | S/S 410 | Carbon Steel | S/S 410 | Carbon Steel | S/S 410 | Carbon Steel |
| Fins/cm | 1.58 | 2.37 | 1.58 | 2.37 | 1.58 | 2.37 |
| Fin Height × Thickness (cm) | 1.905 × 0.127 | 1.746 × 0.127 | 1.905 × 0.127 | 1.746 × 0.127 | 1.905 × 0.127 | 1.746 × 0.127 |

Example 2

This example compares the performance of an ammonia plant using the secondary synthesis loop in one or more embodiments as discussed and described above with reference to FIGS. 1-4, relative to performance of a stand-alone "base-case" ammonia plant, without any secondary ammonia synthesis. Table 2 provides data for key process streams indicating performance of the base-case plant. Table 3 provides data illustrating performance of an ammonia plant in which the ammonia production from the primary synthesis loop 110 can be supplemented with the secondary synthesis 105. In the Table 3 process, stream 12 supplies a portion of the purge stream 156 to the secondary synthesis in the modified package boiler unit 10. Without the secondary synthesis 105 in the base-case system of Table 2, the whole purge stream 156 can be supplied to hydrogen recovery unit 330.

A comparison of Tables 2a, 2b, 3a, and 3b shows that total ammonia production with secondary conversion increases by about 5 percent over the base case, while waste gas flow can be reduced by about 8 percent. The makeup syngas feed increases compared to the base case, due to the recycle of unreacted syngas from the secondary conversion into the mixed feed for reforming.

TABLE 2a

Base Case Ammonia Plant Without Secondary Synthesis

|  | Stream Description | | | | |
|---|---|---|---|---|---|
|  | Makeup Syngas | LP H2 Recycle | Reactor Product Stream: | HP H2 Recycle | Recycle Gas |
|  | 132 | 134 | 142 | 136 | 138 |
|  | Composition (Dry Mole %) | | | | |
| H2 | 71.04 | 77.94 | 48.34 | 81.15 | 57.2 |
| N2 | 27.77 | 20.68 | 27.88 | 17.3 | 32.98 |
| CH4 | 0.85 | 0.55 | 3.93 | 0.74 | 4.64 |
| AR | 0.33 | 0.82 | 1.86 | 0.81 | 2.20 |
| NH3 | 0 | 0 | 18 | 0 | 2.99 |
| Dry Flow (kg-) | 9,860 | 114 | 29,307 | 1,217 | 22,798 |
| Dry Flow (kg/h) | 93,503 | 887 | 387,452 | 8,431 | 285,482 |
| H2O (kg-mol/h) | 0.0 | 0.0 | 0.0 | 0.0 | 0.0 |
| Total Flow (kg-) | 9,860 | 114 | 29,307 | 1,217 | 22,798 |
| Total Flow | 93,503 | 887 | 387,452 | 8,431 | 285,482 |
| Temperature (° C.) | 4 | 19 | 453 | 17 | 25 |
| Pressure (MPa) | 3.58 | 3.65 | 8.86 | 8.49 | 8.58 |
| Density (g/cm3) | 0.015 | 0.012 | 0.019 | 0.023 | 0.042 |
| Average MW | 9.4 | 7.8 | 13.2 | 6.9 | 12.5 |

TABLE 2b

Base Case Ammonia Plant Without Secondary Synthesis

Stream Description

| | Purge Feed | Split to 2° Synthesis | Syngas from 2° Synthesis | NH₃ Product | Waste Gas |
|---|---|---|---|---|---|
| Stream: | 156 | 157 | 170 | 146 | 160 |
| | | Composition (Dry Mole %) | | | |
| H2 | 58.96 | | | 0 | 8.67 |
| N2 | 33.99 | | | 0 | 71.47 |
| CH4 | 4.76 | | | 0 | 14.27 |
| AR | 2.26 | | | 0 | 5.60 |
| NH3 | 0 | | | 100 | 0 |
| Dry Flow (kg- | 1,897 | | | 4,594 | 584 |
| Dry Flow (kg/h) | 23,496 | | | 78,232 | 14,427 |
| H2O (kg-mol/h) | 0.8 | | | 0.6 | 0.0 |
| Total Flow (kg- | 1,898 | | | 4,594 | 584 |
| Total Flow (kg/h) | 23,511 | | | 78,241 | 14,429 |
| Temperature (° C.) | 24 | | | −33 | 23 |
| Pressure (MPa) | 8.52 | | | 0.39 | 0.34 |
| Density (g/cm3) | 0.041 | | | 0.68 | 0.004 |
| Average MW | 12.4 | | | 17.0 | 24.8 |

TABLE 3a

Ammonia Plant With Secondary Synthesis

Stream Description

| | Makeup Syngas | LP H2 Recycle | Reactor Product | HP H2 Recycle | Recycle Gas |
|---|---|---|---|---|---|
| Stream: | 132 | 134 | 142 | 136 | 138 |
| | | Composition (Dry Mole %) | | | |
| H2 | 69.60 | 78.40 | 48.7 | 80.35 | 57.78 |
| N2 | 28.58 | 20.88 | 27.87 | 17.82 | 33.06 |
| CH4 | 1.14 | 1.14 | 3.17 | 0.56 | 3.76 |
| AR | 0.68 | 0.68 | 2.05 | 0.93 | 2.43 |
| NH3 | 0.0 | 0.0 | 18.2 | 0.34 | 2.99 |
| Dry Flow (kg- | 11,819 | 108 | 29,100 | 1,167 | 20,788 |
| Dry Flow (kg/h) | 116,562 | 857 | 384,630 | 8,269 | 259,999 |
| H2O (kg-mol/h) | 3.0 | 0.0 | 0.0 | 0.0 | 0.0 |
| Total Flow (kg- | 11,822 | 105 | 29,100 | 1,167 | 20,788 |
| Total Flow (kg/h) | 116,616 | 803 | 384,630 | 8,269 | 259,999 |
| Temperature (° C.) | −1 | 17 | 455 | 17 | −23 |
| Pressure (MPa) | 3.62 | 3.65 | 8.86 | 8.48 | 8.64 |
| Density (g/cm3) | 0.015 | 0.012 | 0.019 | 0.025 | 0.051 |
| Average MW | 9.9 | 7.9 | 13.2 | 7.1 | 12.5 |

TABLE 3b

Ammonia Plant With Secondary Synthesis

Stream Description

| | Recycle Gas | Purge Feed | Split to 2° Synthesis | Syngas from 2° Synthesis | NH₃ Product | Waste Gas |
|---|---|---|---|---|---|---|
| Stream: | 138 | 156 | 157 | 170 | 146 | 160 |
| | | Composition (Dry Mole %) | | | | |
| H2 | 57.78 | 59.55 | 59.55 | 56.06 | 0 | 8.95 |
| N2 | 33.06 | 34.08 | 34.08 | 36.07 | 0 | 72.84 |
| CH4 | 3.76 | 3.88 | 3.88 | 4.73 | 0 | 11.88 |
| AR | 2.43 | 2.5 | 2.5 | 3.06 | 0 | 6.32 |
| NH3 | 2.99 | 0 | 0 | 0.07 | 100 | 0.01 |
| Dry Flow (kg- | 20,788 | 1,787 | 1,834 | 1,500 | 4,840 | 528 |
| Dry Flow (kg/h) | 259,999 | 22,106 | 22,680 | 19,845 | 82,428 | 13,215 |

TABLE 3b-continued

Ammonia Plant With Secondary Synthesis

| | Recycle Gas | Purge Feed | Split to 2° Synthesis | Syngas from 2° Synthesis | NH₃ Product | Waste Gas |
|---|---|---|---|---|---|---|
| Stream: | 138 | 156 | 157 | 170 | 146 | 160 |
| Composition (Dry Mole %) | | | | | | |
| H2O (kg-mol/h) | 0.0 | 0.0 | 0.0 | 7.7 | 0.6 | 0.0 |
| Total Flow (kg- | 20,788 | 1,787 | 1,834 | 1,508 | 4,840 | 528 |
| Total Flow | 259,999 | 22,106 | 22,680 | 19,984 | 82,437 | 13,215 |
| Temperature | −23 | 25 | 25 | 72 | −33 | 25 |
| Pressure (MPa) | 8.64 | 8.49 | 7.93 | 7.58 | 0.39 | 0.25 |
| Density (g/cm3) | 0.051 | 0.041 | 0.041 | 0.034 | 0.677 | 0.002 |
| Average MW | 12.5 | 12.4 | 12.4 | 13.3 | 17.0 | 25.0 |

Example 3

Table 4 presents one embodiment of operating conditions in a series of synthesis reactors and process heat exchangers in the exhaust duct 16 of a package boiler 10 as in FIG. 1. A syngas preheater 14, two ammonia synthesis reactors 22, 24, and three BFW heaters 30, 32, 34 can be alternately arrayed in the exhaust duct 16 for heat rejection and recovery. The conditions correspond to the process of Table 3 in the operating configuration of Example 2 and FIG. 3.

TABLE 4

Package Boiler-Secondary Ammonia Converter Operation

| | | Temperature (° C.) | | | | Pressure Drop | |
|---|---|---|---|---|---|---|---|
| | Heat Duty | Process Fluid | | Exhaust Gas | | Process Fluid | Exhaust Gas |
| Process Unit | (MJ/h) | inlet | outlet | inlet | outlet | kPa | mm Hg |
| Syngas Preheater 14 | 1,772 | 382 | 413 | 434 | 423 | 4.1 | 1.15 |
| BFW Heater 34 | 9,514 | 207 | 224 | 423 | 366 | 7.5 | 0.59 |
| Reactor 22 | 4,820 | 413 | 413 | 366 | 395 | n/a | 3.19 |
| BFW Heater 32 | 4,304 | 199 | 207 | 395 | 369 | 3.5 | 0.30 |
| Reactor 24 | 4,504 | 413 | 413 | 369 | 396 | n/a | 3.20 |
| BFW Heater 30 | 35,948 | 130 | 198 | 396 | 173 | 44.8 | 2.75 |

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for producing one or more products from syngas comprising:
    gasifying a feedstock in the presence of an oxidant to provide a syngas comprising carbon dioxide, carbon monoxide, and hydrogen;
    combusting at least a portion of the syngas to provide an exhaust gas;
    introducing at least a portion of the exhaust gas to a channel having one or more reaction zones at least partially disposed therein, wherein the one or more reaction zones are in indirect heat exchange with the exhaust gas, and wherein the one or more reaction zones comprises one or more catalyst-containing tubes; and
    reacting a reactant in at least one of the one or more reaction zones to provide one or more reactor products.

2. The process of claim 1, wherein the reaction is endothermic and heat from the exhaust gas is used to provide heat to the reaction.

3. The process of claim 1, wherein the reaction is exothermic and the exhaust gas removes the heat of reaction.

4. The process of claim 1, wherein at least a portion of the syngas is introduced to at least one of the reaction zones to provide methanol, alkyl formates, dimethyl ether, ammonia, Fischer-Tropsch products, methane, derivatives thereof, or combinations thereof.

5. The process of claim 1, wherein the syngas is combusted in a combustion turbine.

6. The process of claim 1, wherein two or more reaction zones are at least partially disposed within the channel, and wherein the two or more reaction zones are arranged in parallel fluid communication, serial fluid communication, or a combination thereof.

7. The process of claim 1, wherein the catalyst comprises iron, ruthenium, cobalt, rhodium, iridium, nickel, palladium, platinum, copper, zinc, cadmium, aluminum, oxides thereof, derivatives thereof, or combinations thereof.

8. The process of claim 1, wherein at least one of the one or more catalyst-containing tubes comprises straight tubes, U-tubes, coiled tubes, bayonet tubes, surface enhanced tubes, or a combination thereof.

9. The process of claim 1, wherein the feedstock comprises biomass, coal, oil shale, coke, tar, asphaltenes, low ash polymers, no ash polymers, hydrocarbon-based polymeric materials, biomass derived material, by-product derived material from manufacturing operations, derivatives thereof, or combinations thereof.

10. The process of claim 1, wherein the reactant comprises hydrogen, carbon monoxide, carbon dioxide, nitrogen, alkenes, alkanes, aromatics, or combinations thereof.

11. A process for producing one or more products from syngas comprising: combining one or more feedstocks and one or more oxidants in a fluidized reaction zone to provide a syngas; combusting at least a portion of the syngas to provide an exhaust gas; introducing at least a portion of the exhaust gas to a channel having one or more reaction zones and one or more heat exchange zones at least partially disposed therein, wherein the one or more reaction zones and one or more heat exchange zones are in indirect heat exchange with the turbine exhaust gas, wherein the one or more reaction zones comprises one or more catalyst-containing tubes; and reacting at least a portion of a reactant in at least one of the one or more reaction zones to provide one or more products.

12. The process of claim 11, wherein the fluidized reaction zone is operated at a temperature of from 550.degree. C. to 1,050.degree. C.

13. The process of claim 11, wherein the syngas is combusted in a combustion turbine.

14. The process of claim 11, wherein the reaction is endothermic and heat from the exhaust gas is used to provide heat to the reaction.

15. The process of claim 11, wherein the reaction is exothermic and the exhaust gas removes the heat of reaction.

* * * * *